United States Patent
Akiyama et al.

(10) Patent No.: US 7,441,895 B2
(45) Date of Patent: Oct. 28, 2008

(54) SPECTACLE LENS SUPPLY SYSTEM, SPECTACLE WEARING PARAMETER MEASUREMENT APPARATUS, SPECTACLE WEARING TEST SYSTEM, SPECTACLE LENS, AND SPECTACLE

(75) Inventors: Hisanori Akiyama, Tokyo (JP); Masahiro Jinbo, Tokyo (JP); Yasunori Ueno, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 10/581,966

(22) PCT Filed: Mar. 25, 2005

(86) PCT No.: PCT/JP2005/005521

§ 371 (c)(1), (2), (4) Date: Jul. 5, 2006

(87) PCT Pub. No.: WO2005/092173

PCT Pub. Date: Oct. 6, 2005

(65) Prior Publication Data

US 2007/0118428 A1    May 24, 2007

(30) Foreign Application Priority Data

| Mar. 26, 2004 | (JP) | ............................. 2004-091629 |
| Mar. 26, 2004 | (JP) | ............................. 2004-091648 |
| Mar. 26, 2004 | (JP) | ............................. 2004-091670 |

(51) Int. Cl.
*A61B 3/14* (2006.01)
(52) U.S. Cl. ...................................... 351/206; 351/178
(58) Field of Classification Search .................. 351/204, 351/177, 178; 623/205–221
See application file for complete search history.

(56) References Cited

U.S. PATENT DOCUMENTS

| 5,617,155 A | 4/1997 | Ducarouge et al. |
| 6,533,418 B1 * | 3/2003 | Izumitani et al. ............ 351/204 |
| 2001/0051953 A1 | 12/2001 | Fukuma et al. |

FOREIGN PATENT DOCUMENTS

| JP | A 8-47481 | 2/1996 |
| JP | B2 2982991 | 9/1999 |
| JP | A 2000-122011 | 4/2000 |
| JP | A 2002-10977 | 1/2002 |
| JP | A 2002-10981 | 1/2002 |
| WO | WO 98/52092 | 11/1998 |

* cited by examiner

*Primary Examiner*—Darryl J Collins
(74) *Attorney, Agent, or Firm*—Oliff & Berridge, PLC

(57) ABSTRACT

Aims to enable to supply an optimal and dedicated spectacle lens or spectacle for each spectacle wearer, and also to verify a spectacle wearing state appropriately.

A spectacle wearing parameter measurement system, sets a spectacle wearer to be in a distance vision state or a near vision state in which, in the near vision state, at least, one of an eyeball rotation angle and a near vision target distance is changeable optionally; takes an image of the spectacle wearer set in the distance vision state or near vision state by an image pickup device; imports the image; and measures and calculates a spectacle wearing parameter based on the image. A server computer of a factory received the image uses the image data to manufacture a spectacle lens or a spectacle. Further, a spectacle wearing test system verifies whether or not a spectacle wearing state is appropriate based on a figure obtained by a comparison comparing a spectacle wearing parameter measured at present time after manufacturing the spectacle and the spectacle wearing parameter before manufacturing the spectacle.

10 Claims, 20 Drawing Sheets

FIG. 6
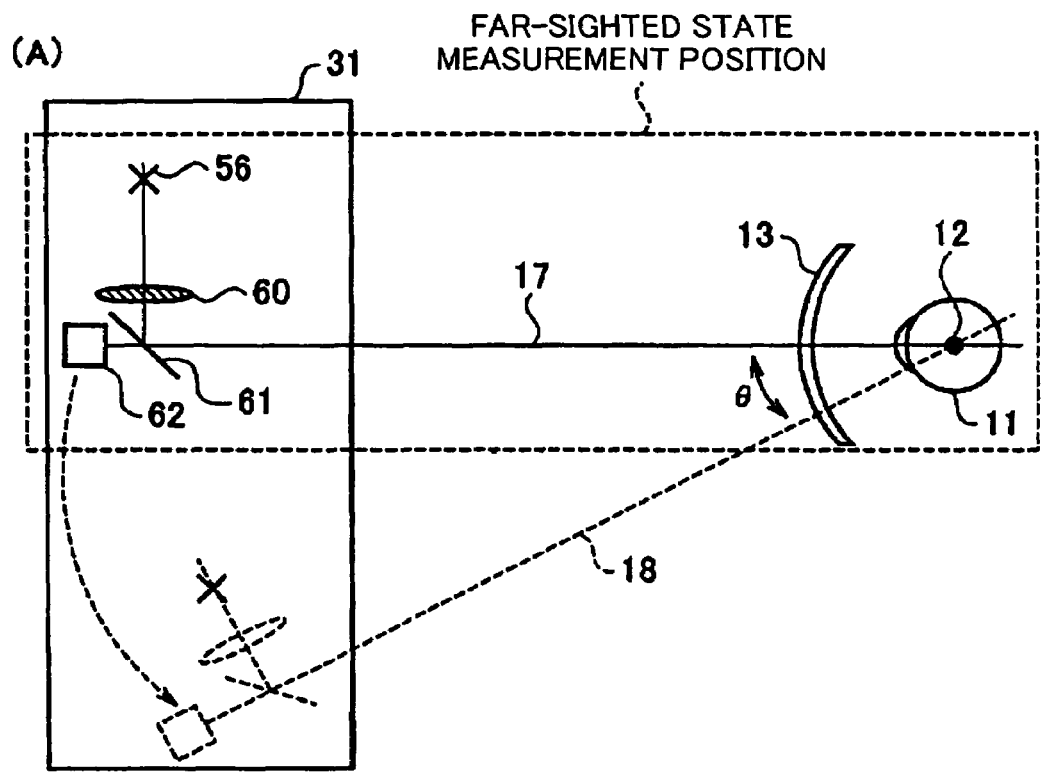
(A) FAR-SIGHTED STATE MEASUREMENT POSITION
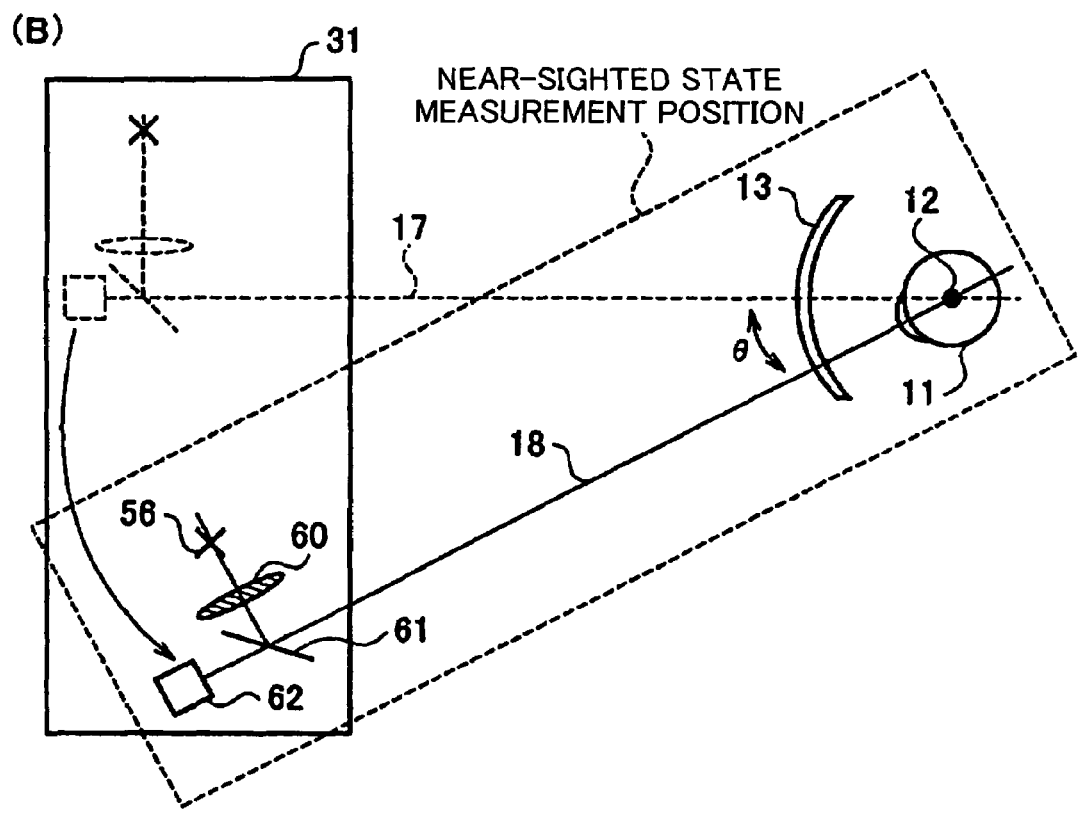
(B) NEAR-SIGHTED STATE MEASUREMENT POSITION

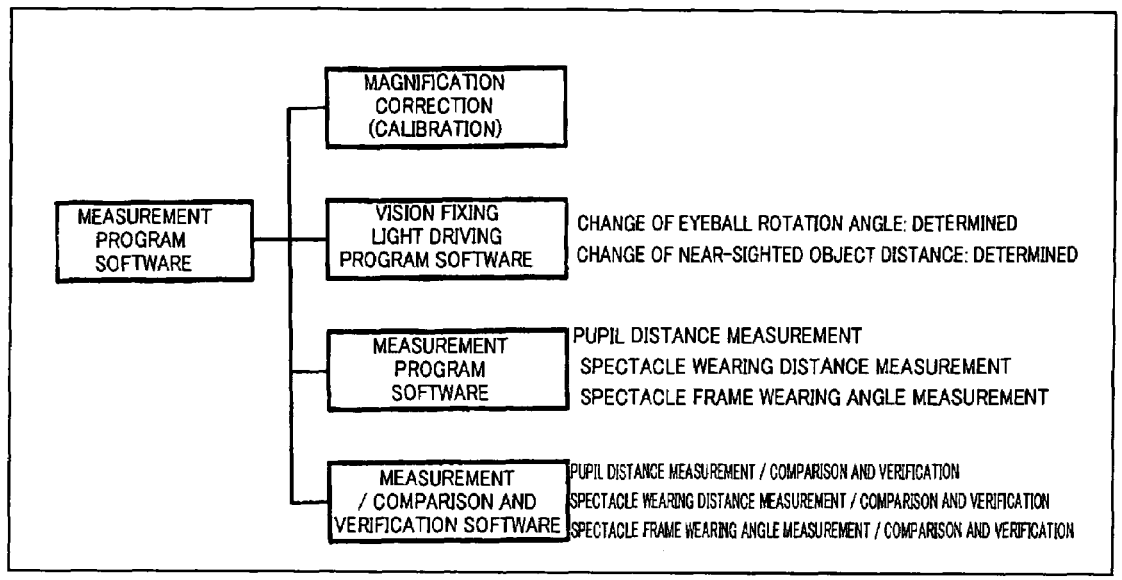

FIG. 16
(A) MEASUREMENT SCREEN
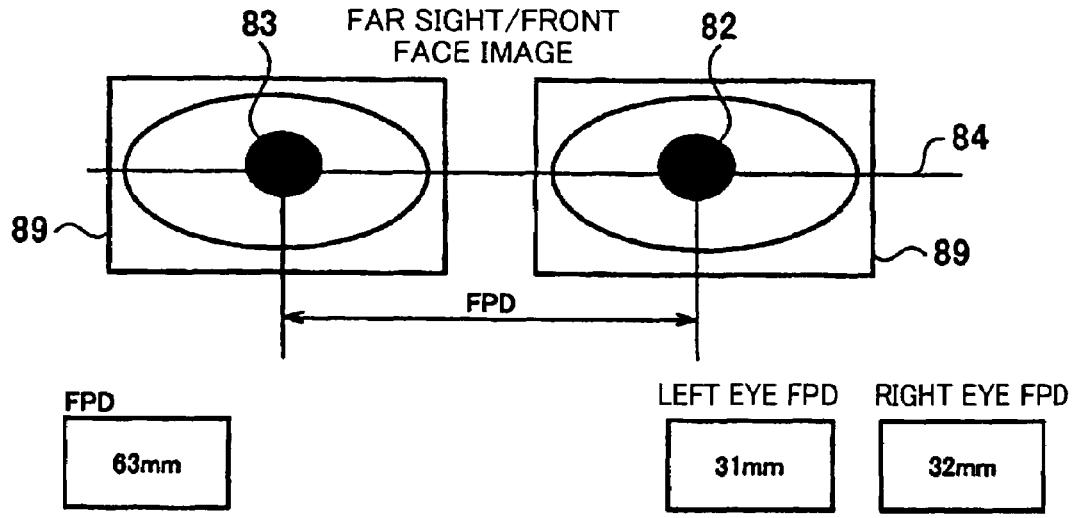
(B) LIGHT AMOUNT DISTRIBUTION
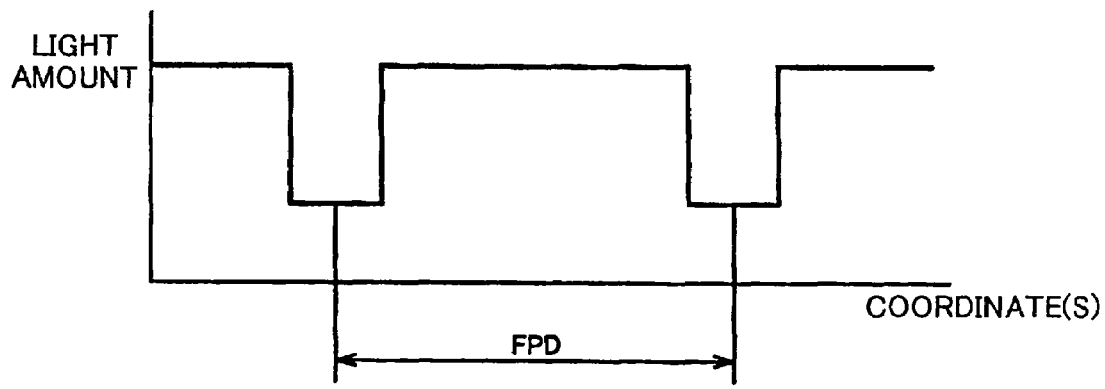
(C) COMPARISON SCREEN
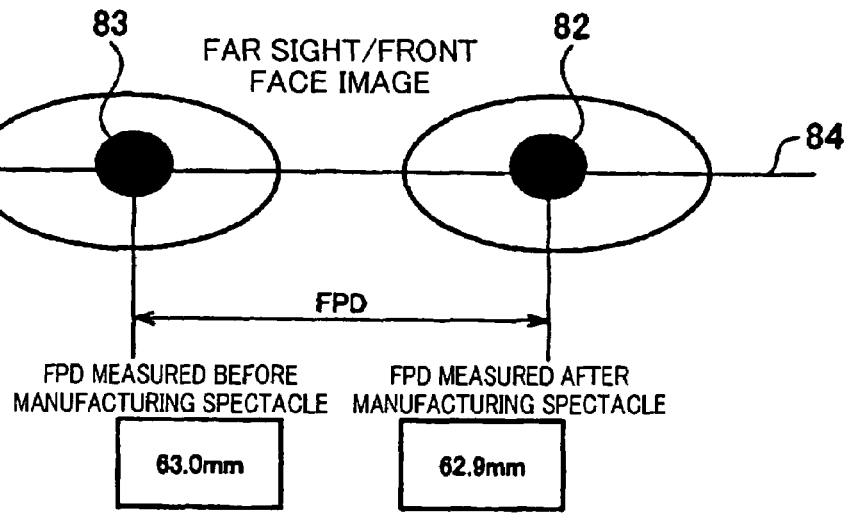

FIG. 18
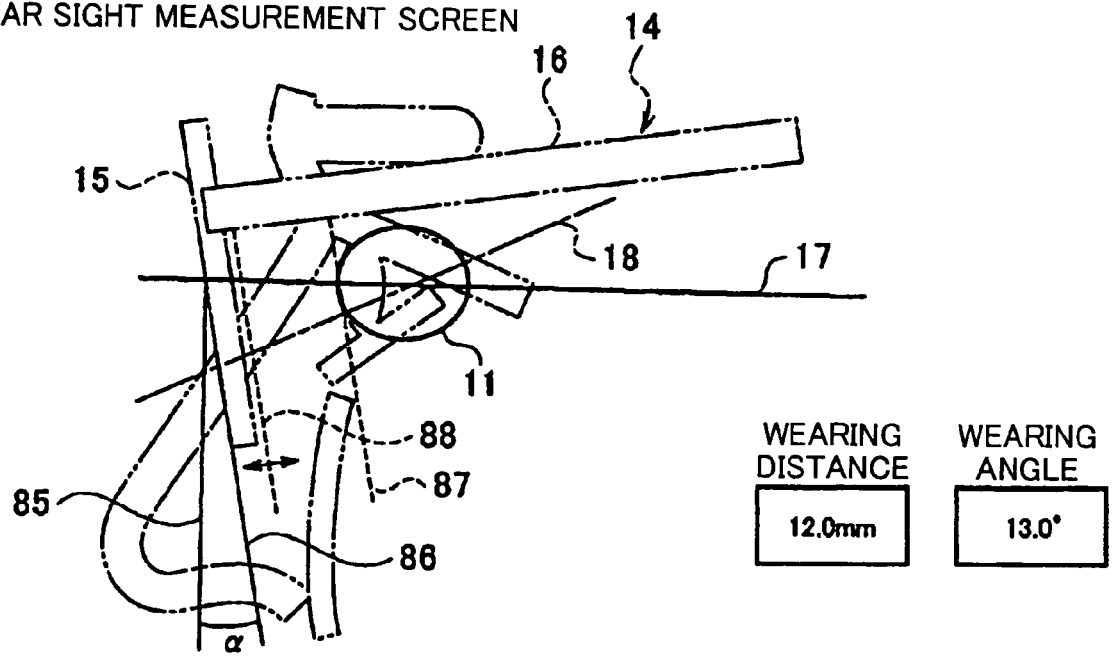
(A) MEASUREMENT SCREEN
FAR SIGHT MEASUREMENT SCREEN
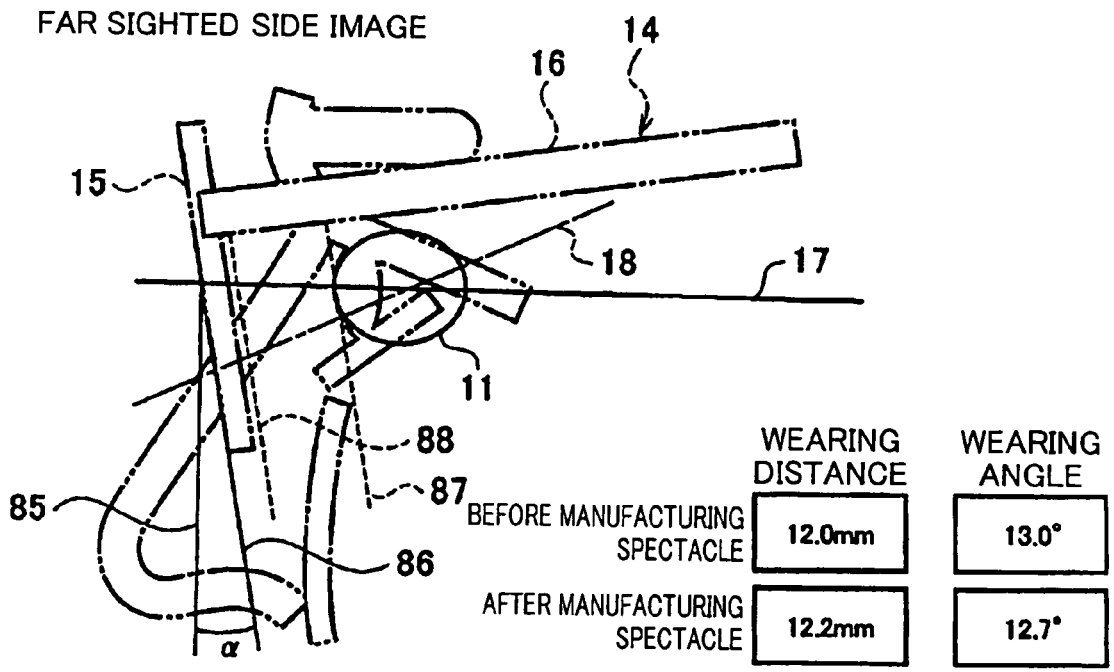
(B) COMPARISON SCREEN
FAR SIGHTED SIDE IMAGE

FIG. 19

| | STORAGE SCREEN | | |
|---|---|---|---|
| VISIT DATE | 1  Jan | ADDRESS | 〒 3-3-3, OO-CHO, SHINJUKU-KU, TOKYO, 160-8888 JAPAN |
| CUSTOMER ID NUMBER | 00000001 | TEL | 03-xxx-xxx |
| KANA | TARO  HOYA | E-MAIL | abcdefg@xx.ne.jp |
| NAME | TARO  HOYA | | |
| GENDER | MALE | | Memo |
| BIRTH DATE | JANUARY  1  1950 | | |

| | FRAME 1 | | FRAME 2 | |
|---|---|---|---|---|
| NEAR-SIGHTED DISTANCE | 00 | mm | 00 | mm |
| NEAR-SIGHTED ANGLE | 0 | ° | 0 | ° |
| PROGRESSIVE ZONE LENGTH | 00 | mm | 00 | mm |
| WEARING DISTANCE / FAR SIGHT | 00 | mm | 00 | mm |
| WEARING DISTANCE / NEAR SIGHT | 00 | mm | 00 | mm |
| RIGHT EYE PD | 00 | mm | 00 | mm |
| LEFT EYE PD | 00 | mm | 00 | mm |
| BOTH EYES PD | 00 | mm | 00 | mm |
| FRAME TYPE | METAL | | CELL | |

STORAGE

X { (customer info section)
Y { (frame measurement section)
Z { (bottom section)

FAR-SIGHTED SIDE FACE IMAGE

FIG. 25

(A) CUSTOMER INDIVIDUAL DATA

| ID NUMBER | 111-111-11111 |
|---|---|
| NAME | TARO HOYA |
| GENDER | MALE |
| TELEPHONE | 03-×××-×××× |
| E-MAIL | abcdefg@**.ne.jp |
| ADDRESS | 3-3-3, OO-CHO, SHINJUKU-KU, TOKYO |
| BIRTH DATE | JAN 1, 1950 |
| AGE | 54 |
| OCCUPATION | COMPANY EMPLOYEE |
| KIND OF OCCUPATION | GENERAL AFFAIRS DEPT. |
| INTEREST | GOLF, DRIVE |
| ORDER RECEPTION LABORATORY | LABORATORY IN xx TOWN |
| ORDERING DATE | APRIL 1, 2004 |
| ORDERING SOURCE | SPECTACLE SHOP IN xx TOWN |
| ADDRESS OF ORDERING SOURCE | 1-1-1, OO-CHO, SHINJUKU-KU, TOKYO |
| TELEPHONE NUMBER OF ORDERING SOURCE | 03-×××-×××× |

⎫X (B) FIRST REGISTERED PRESCRIPTION

| CLASSIFICATION | PRESBYOPIA, MYOPIA, ASTIGMATISM |
|---|---|
| CHIEF COMPLAINT | DIOPTER BECOMES NOT MATCHED |
| PURPOSE OF USE | FOR DAILY LIFE |
| ORDER FREQUENCY | FIRST TIME |

| LENS PRODUCT NAME | LENS MATERIAL NAME | LENS REFRACTIVE POWER | COATING |
|---|---|---|---|
| ABC | HN-5 | 1.600 | MULTI-LAYERED COAT |

⎫W

| | SPH | CYL | AXS | ADD | PX | PY | FPD | NPD | FVD | NVD | RA | ST | ODS |
|---|---|---|---|---|---|---|---|---|---|---|---|---|---|
| R | -1.00 | -0.50 | 180 | 2.00 | 0.00 | 0.00 | 32 | 29.5 | 12 | 14 | 30 | 12 | 350 |
| L | -1.25 | -0.75 | 5 | 2.00 | 0.00 | 0.00 | 31 | 28.5 | 12 | 14 | 30 | 12 | 350 |

Y: SPH, CYL, AXS, ADD, PX, PY
V: FPD, NPD, FVD, NVD, RA, ST, ODS

Z { | FRAME MODEL NUMBER | 123T456 | FRAME NAME | FIELD MASTER |

SPECTACLE LENS SUPPLY SYSTEM, SPECTACLE WEARING PARAMETER MEASUREMENT APPARATUS, SPECTACLE WEARING TEST SYSTEM, SPECTACLE LENS, AND SPECTACLE

TECHNICAL FIELD

The present invention relates to a spectacle lens supply system, and particularly, to a spectacle lens supply system in which a computer set at an order-placement side of a spectacle lens or a spectacle and a computer set at a manufacturing side of the spectacle lens or the spectacle are connected in an information exchangeable manner.

Further, the present invention relates to a spectacle wearing parameter measurement apparatus taking an image of a spectacle wearer wearing the spectacle to measure a variety of spectacle wearing parameters required to manufacture the spectacle from the image and the spectacle lens and the spectacle manufactured based on the spectacle wearing parameters measured by the measurement apparatus.

Still further, the present invention relates to a spectacle wearing test system verifying a spectacle wearing state by comparing a spectacle wearing parameter measured in advance and stored in a customer database and a spectacle wearing parameter of the same spectacle wearer measured at present time, for example, a spectacle wearing parameter measured when the same spectacle wearer wears the spectacle manufactured based on the above-described stored spectacle wearing parameter.

BACKGROUND ART

Conventionally, it is known for a spectacle lens supply system receiving or placing an order for a spectacle lens or the like online (see Patent document 1). The conventional system includes an order-placement side computer set at an order-placement side of the spectacle lens, and a manufacturing side computer connected to the order-placement side computer in an information exchangeable manner and executing an order receiving such as to obtain lens design data based on order information such as spectacle prescription data and the like transmitted from the order-placement side computer. These order-placement side computer and the manufacturing side computer calculate in response to a predetermined input operation to perform a processing required to receive or place the order while exchanging information with each other

[Patent Document 1] Japanese Patent Publication No. 2982991

In the spectacle fabrication, it is necessary to perform an optical designing in accordance with various spectacle wearing parameters related to a spectacle prescription value, a spectacle frame selection, and a spectacle wearer, and to edge the spectacle lens manufactured based on the design value to be set in the spectacle frame shape. As the spectacle wearing parameters related to the spectacle wearer, there are a distance vision inter-pupil distance, a near vision inter-pupil distance, a distance vision spectacle wearing distance (distance between vertexes), a spectacle frame wearing angle, and so on.

Conventionally, as spectacle wearing parameter measurement methods, various optical measurement methods are known.

For instance, spectacle stores largely use a pupil-meter (PD meter) to measure the distance vision inter-pupil distance and the near vision inter-pupil distance as the spectacle wearing parameters. This method can obtain values of a certain level of accuracy; however, it forces the spectacle wearer to be in an uncomfortable body position and makes the spectacle wearer look through a test apparatus, so that measurement values are varied, differently from a natural spectacle wearing conditions.

As an apparatus bringing a solution to such a problem, it is known for a Video-Infral of Carl Zeiss described in Patent document 2. The apparatus is used in the spectacle store and obtains a front image and a side image of the spectacle wearer by using two units of video camcorders and a reflector. In order to determine a center position of the eye of the spectacle wearer, a tangent line contacting a spectacle frame shape is traced in a rectangular shape on the screen using a mouse-type pointing device. After that, in the front image screen of the spectacle wearer, a relative position of the pupil of the spectacle wearer with respect to the spectacle frame, namely, the distance vision inter-pupil distance as the spectacle wearing parameter is measured. Further, in the side image screen of the spectacle wearer, a tilt angle of the spectacle frame based on a vertical line as a reference (namely, a spectacle frame wearing angle as the spectacle wearing parameter), and a distance between vertexes being a distance to a cornea vertex based on the position of the spectacle frame as a reference (namely, the distance vision spectacle wearing distance as the spectacle wearing parameter) are measured.

[Patent document 2] Japanese Patent Application Laid-Open No. Hei8-47481 (page 3)

DISCLOSURE OF THE INVENTION

Problems to Be Solved by the Invention

However, the above-described conventional system is a system to place or receive an order for a spectacle lens, and does not measure the spectacle wearing parameter in accordance with the respective spectacle wearer, does not perform an optical designing using the measured value, does not process, and does not provide an optimal for and dedicated spectacle lens to the respective spectacle wearers.

According to the conventional apparatus described in Patent document 2, mainly, the distance vision inter-pupil distance, the spectacle frame wearing angle, and the inter-vertex distance are measured, however, the inter-vertex distance out of these does not consider a three dimensional shape of the spectacle frame, so that it can not be said to be the distance vision spectacle wearing distance as a spectacle wearing parameter, practically, and the figure can not be effectively used. In other words, in order to measure and calculate the distance vision spectacle wearing distance and the near vision spectacle wearing distance as spectacle wearing parameters, a data related to the three dimensional shape of the spectacle frame such as a frame horizontal tilt angle is necessary, and there is no apparatus so far that uses the data to measure and calculate the distance vision spectacle wearing distance ant the near vision spectacle wearing distance.

Further, in the apparatus described in Patent document 2, the near vision spectacle wearing distance being a spectacle wearing parameter related to a near vision, which is required by a spectacle lens such as a progressive power lens, the eyeball rotation angle in the near vision state, and the near vision target distance can not be measured and set. Further, conventionally, there is no apparatus that changes the eye rotation angle and near vision target distance in the near vision state in accordance with the spectacle wearer to detect an optimal near vision state for the spectacle wearer and to thereby pickup the image of the spectacle wearer in that state.

Furthermore, there is no apparatus capable of performing a measurement by selecting a spectacle wearing parameter required to manufacture a refractive power correction spectacle lens (progressive power lens, multifocal lens, single vision lens for near vision, single vision lens, and so forth) in accordance with the prescription of each spectacle wearer.

Moreover, there is no apparatus capable of verifying a wearing state of a spectacle by comparing spectacle wearing parameters measured before and after manufacturing the spectacle with respect to a spectacle wearer wearing the spectacle.

In consideration of the above circumstance, a first object of the present invention is to provide a spectacle lens supply system capable of supplying an optimal and dedicated spectacle lens or spectacle for each of spectacle wearers.

A second object of the present invention is to provide a spectacle lens supply system functioning effectively when the spectacle wearer makes an order again for a new spectacle or for a spectacle based on a different prescription, or when an order placement side such as a spectacle store updates its historical data related to the spectacle of its customer being a spectacle wearer.

A third object of the present invention is to provide a spectacle lens enabled to be an optimal and dedicated spectacle lens for each of spectacle wearers.

A forth object of the present invention is to provide a spectacle enabled to be an optimal and dedicated spectacle for each of spectacle wearers.

A fifth object of the present invention is to provide a spectacle wearing parameter measurement apparatus capable of measuring a spectacle wearing parameter required to manufacture a spectacle with high accuracy, the spectacle wearing parameter enabling to manufacture an optimal and dedicated spectacle lens or spectacle for each of spectacle wearers.

A sixth object of the present invention is to provide a spectacle lens enabled to be an optimal and dedicated spectacle for each of spectacle wearers based on a spectacle wearing parameter measured by a spectacle wearing parameter measurement apparatus with high accuracy.

A seventh object of the present invention is to provide a spectacle enabled to be an optimal and dedicated spectacle for each of spectacle wearers based on a spectacle wearing parameter measured by a spectacle wearing parameter measurement apparatus with high accuracy.

An eighth object of the present invention is to provide a spectacle wearing test system capable of verifying a wearing state of a spectacle appropriately.

A ninth object of the present invention is to provide a spectacle wearing test system capable of verifying a wearing state of a manufactured spectacle.

Means for Solving the Problems

A spectacle lens supply system according to the invention described in Claim 1 is a spectacle lens supply system supplying a spectacle lens or a spectacle, including a manufacturing-side computer performing a process required for receiving an order based on order information on the spectacle lens, in which the manufacturing-side computer is configured to be able to, at least, receive or be inputted personal data of each spectacle wearer required to manufacture the spectacle and including a spectacle wearing parameter, and in which the spectacle wearing parameter is, at least, one of a distance vision inter-pupil distance, a near vision inter-pupil distance, a distance vision spectacle wearing distance, a near vision spectacle wearing distance, a spectacle frame wearing angle, an eyeball rotation angle, an eyeball rotation angle and a near vision target distance.

A spectacle lens supply system according to the invention described in Claim 1 is a spectacle lens supply system, including: an order-placement side computer disposed on the order placement side of an spectacle lens; and a manufacturing side computer connected to the order-placement side computer in an information exchangeable manner, in which the order-placement side computer and the manufacturing side computer perform a process required for making and receiving an order for a spectacle lens by exchanging information with each other to supply the spectacle lens or a spectacle, in which a spectacle wearing parameter measurement apparatus measuring a spectacle wearing parameter of each spectacle wearer is connected to the order-placement side computer, and the order-placement side computer is configured to be, at least, transmittable a personal data of each spectacle wearer required to manufacture the spectacle including the spectacle wearing parameter, and in which the spectacle wearing parameter is, at least, one of a distance vision inter-pupil distance, a near vision inter-pupil distance, a distance vision spectacle wearing distance, a near vision spectacle wearing distance, a spectacle frame wearing angle, an eyeball rotation angle and a near vision target distance.

A spectacle lens supply system according to the invention described in Claim 3 is the spectacle lens supply system described in claim 1, in which the manufacturing side computer has a customer database and the personal data of each spectacle wearer required to manufacture the spectacle including the spectacle wearing parameter is recorded and stored in the customer database.

A spectacle lens supply system according to the invention described in Claim 4 is the spectacle lens supply system described in claim 2, in which, at least, one of the order-placement side computer and the manufacturing side computer has a customer database and the personal data of each spectacle wearer required to manufacture the spectacle including the spectacle wearing parameter is recorded and stored in the customer database.

A spectacle lens supply system according to Claim 5 is the spectacle lens supply system described in any one of claim 1 to claim 4, in which the personal data of each spectacle wearer required to manufacture the spectacle includes, at least, one of spectacle lens data, spectacle frame data, spectacle prescription data, processing instruction data and a spectacle wearing parameter.

A spectacle lens according to the invention described in Claim 6 is a spectacle lens processed in a spectacle lens supply system described in any one of claim 1 to claim 5, characterized in that the spectacle lens being manufactured through an optical designing using personal data of each spectacle wearer required to manufacture a spectacle including a spectacle wearing parameter.

A spectacle according to the invention described in Claim 7 is a spectacle processed in a spectacle lens supply system described in any one of claim 1 to claim 5, characterized in that the spectacle lens being manufactured using personal data of each spectacle wearer required to manufacture a spectacle including a spectacle wearing parameter.

A spectacle wearing test system according to the invention described in Claim 8 is a spectacle wearing test system including: a spectacle wearing parameter measurement apparatus measuring a spectacle wearing parameter required to manufacture a spectacle suited to a spectacle wearer; a first spectacle wearing parameter acquisition means acquiring the spectacle wearing parameter before manufacturing the spectacle of the spectacle wearer; a second spectacle wearing parameter acquisition means acquiring the spectacle wearing parameter after manufacturing the spectacle of the spectacle wearer; and a comparison means making comparison between the spectacle wearing parameters acquired by the first spectacle wearing parameter acquisition means and the second spectacle wearing parameter acquisition means using figures, in which the spectacle wearing parameter measured by the spectacle wearing parameter measurement apparatus is, at least, one of a distance vision inter-pupil distance, a near vision inter-pupil distance, a distance vision spectacle wearing distance, a near vision spectacle wearing distance, a spectacle frame wearing angle, an eyeball rotation angle and a near vision target distance.

A spectacle wearing test system according to the invention described in Claim 9 is a spectacle wearing test system including: a spectacle wearing parameter measurement apparatus measuring a spectacle wearing parameter required to manufacture a spectacle suitable for a spectacle wearer; a first spectacle wearing parameter acquisition means acquiring the spectacle wearing parameter before manufacturing the spectacle of the spectacle wearer; a second spectacle wearing parameter acquisition means acquiring the spectacle wearing parameter after manufacturing the spectacle of the spectacle wearer; a comparison means making comparison between the spectacle wearing parameters acquired by the first spectacle wearing parameter acquisition means and the second spectacle wearing parameter acquisition means using figures; and a verification means verifying by determining whether or not a spectacle wearing state is appropriate based on a figure obtained by the comparison means, in which the spectacle wearing parameter measured by the spectacle wearing parameter measurement apparatus is, at least, one of a distance vision inter-pupil distance, a near vision inter-pupil distance, a distance vision spectacle wearing distance, a near vision spectacle wearing distance, a spectacle frame wearing angle, an eyeball rotation angle and a near vision target distance.

A spectacle wearing test system according to the invention described in Claim 10 is the spectacle wearing test system described in claim 8 or claim 9, further including: customer database connected to the spectacle wearing parameter measurement apparatus in an information exchangeable manner, in which the figure(s) of the spectacle wearing parameter acquired by the first spectacle wearing parameter acquisition means or/and the second spectacle wearing parameter acquisition means is (are) recordable in the customer database, and in which the comparison means makes the comparison between the spectacle wearing parameters of the same spectacle wearer acquired by the first spectacle wearing parameter acquisition means and the second spectacle wearing parameter acquisition means with figures.

A spectacle wearing test system according to the invention described in Claim 11 is a spectacle wearing test system including: a spectacle wearing parameter measurement apparatus measuring a spectacle wearing parameter required to manufacture a spectacle suitable for a spectacle wearer; a memory means connected to the spectacle wearing parameter measurement apparatus in an information exchangeable manner and capable of recording, at least, a spectacle wearing parameter; a spectacle wearing parameter acquisition means acquiring the spectacle wearing parameter from the memory means; and a comparison means comparing the spectacle wearing parameter at present time measured by the spectacle wearing parameter measurement apparatus with the spectacle wearing parameter of the same spectacle wearer acquired by the spectacle wearing parameter acquisition means with figures, in which the spectacle wearing parameter measured by the spectacle wearing parameter measurement apparatus is, at least, one of a distance vision inter-pupil distance, a near vision inter-pupil distance, a distance vision spectacle wearing distance, a near vision spectacle wearing distance, a spectacle frame wearing angle, an eyeball rotation angle and a near vision target distance.

A spectacle wearing parameter measurement apparatus according to the invention described in Claim 12 is a spectacle wearing parameter measurement apparatus measuring a spectacle wearing parameter required to manufacture a spectacle suited to a spectacle wearer, including: a vision fixing means setting the spectacle wearer wearing a spectacle frame to be in a distance vision state or a near vision state and, in the near vision state, at least, one of an eyeball rotation angle and a near vision target distance can be changed optionally, an image input means taking an image of the spectacle wearer set in the distance vision state or the near vision state by the vision fixing means using an image pickup device to import the image; and a measurement and calculation means measuring and calculating the spectacle wearing parameter based on the taken image obtained by the image input means.

A spectacle wearing parameter measurement apparatus according to the invention described in Claim 13 is the spectacle wearing parameter measurement apparatus described in claim 12, in which the spectacle wearing parameter measured and calculated by the measurement and calculation means is, at least, one of a distance vision inter-pupil distance, a near vision inter-pupil distance, a distance vision spectacle wearing distance, a near vision spectacle wearing distance, a spectacle frame wearing angle, an eyeball rotation angle and a near vision target distance.

A spectacle wearing parameter measurement apparatus according to the invention described in Claim 14 is the spectacle wearing parameter measurement apparatus described in claim 12 or claim 13, in which the vision fixing means moves in a rotating manner around a center of rotation of an eyeball by being interlocked with the image pickup device to always keep an optical axis of the image pickup device match with a visual axis of the eyeball.

A spectacle wearing parameter measurement apparatus according to the invention described in Claim 15 is the spectacle wearing parameter measurement apparatus according to any one of claim 12 to claim 14, in which, of the spectacle wearing parameter, the eyeball rotation angle and the near vision target distance are measured by being changed and determined by the vision fixing means while letting the spectacle wearer confirm an appropriate near vision state.

A spectacle wearing parameter measurement apparatus according to the invention described in Claim 16 is the spectacle wearing parameter measurement apparatus described in any one of claim 12 to claim 15, in which, of the spectacle wearing parameter, the distance vision spectacle wearing distance and the near vision spectacle wearing distance are measured by a calculation in consideration of a three dimensional shape of the spectacle frame.

A spectacle wearing parameter measurement apparatus according to the invention described in Claim 17 is the spectacle wearing parameter measurement apparatus described in any one of claim 12 to claim 16, in which, of the spectacle wearing parameter, the near vision inter-pupil distance is measured by a calculation on a spectacle lens surface of the spectacle worn by the spectacle wearer.

A spectacle wearing parameter measurement apparatus according to the invention described in Claim 18 is the spectacle wearing parameter measurement apparatus described in any one of claim 12 to claim 17, in which a vision fixing beam in a distance vision state set by the vision fixing means is formed as a virtual image.

A spectacle wearing parameter measurement apparatus according to the invention described in Claim 19 is the spectacle wearing parameter measurement apparatus described in any one of claim 12 to claim 18, in which the measurement and calculation means detects blinking of the spectacle wearer and takes an image of the spectacle wearer when the spectacle wearer gazes unblinkingly.

A spectacle lens according to the invention described in Claim 20 is a spectacle lens manufactured through an optical designing using, at least, one of spectacle wearing parameters measured by a spectacle wearing parameter measurement apparatus described in any one of claim 12 to claim 19.

A spectacle according to the invention described in Claim 21 is a spectacle manufactured using, at least, one of spectacle wearing parameters measured by a spectacle wearing parameter measurement apparatus described in any one of claim 12 to claim 19.

INDUSTRIAL AVAILABILITY

According to the invention described in Claim 1 or Claim 3, a manufacturing side computer is configured to be able to receive or be inputted personal data of each spectacle wearer required to manufacture a spectacle and including a spectacle wearing parameter, so that an optimal and dedicated spectacle lens or spectacle for the spectacle wearer can be supplied by making use of the data for manufacturing the spectacle lens or spectacle.

According to the invention described in Claim 2, Claim 4, or Claim 5, an order-placement side computer is configured to be able to transmit personal data of each spectacle wearer required to manufacture a spectacle and including a spectacle wearing parameter to a manufacturing side computer, so that an optimal and dedicated spectacle lens or spectacle for the spectacle wearer can be supplied in that the manufacturing side computer receives the personal data of each spectacle wearer required to manufacture the spectacle and including the spectacle wearing parameter from the order-placement side computer to make use of the data for manufacturing the spectacle lens or spectacle.

According to the invention described in Claim 3 or Claim 4, personal data of each spectacle wearer required to manufacture a spectacle and including a spectacle wearing parameter is recorded and stored, at least, one of the customer databases in the manufacturing side computer and in the order-placement side computer, so that the customer database functions effectively when the spectacle wearer makes a new spectacle or a spectacle based on a different prescription, or when an order-placement side such as a spectacle store updates historical data related to a spectacle of the spectacle wearer being a customer.

Further, the personal data of each spectacle wearer required to manufacture the spectacle and including the spectacle wearing parameter are recorded and stored in the customer database, so that an optimal and dedicated spectacle lens or spectacle for the spectacle wearer can be supplied in that the manufacturing side computer makes use of the data in the customer database.

According to the invention described in Claim 6, a spectacle lens is manufactured through an optical designing using personal data of each spectacle wearer required to manufacture a spectacle and including a spectacle wearing parameter, so that the spectacle lens is enabled to be an optimal and dedicated spectacle lens for the spectacle wearer.

According to the invention described in Claim 7, a spectacle is manufactured using personal data of each spectacle wearer required to manufacture a spectacle and including a spectacle wearing parameter, so that the spectacle is enabled to be an optimal and dedicated spectacle for the spectacle wearer.

According to the invention described in Claim 8 or Claim 10, a spectacle wearing test system includes: a spectacle wearing parameter measurement apparatus measuring a spectacle wearing parameter required to manufacture a spectacle suited to a spectacle wearer; a first spectacle wearing parameter acquisition means acquiring the spectacle wearing parameter before manufacturing the spectacle of the spectacle wearer; a second spectacle wearing parameter acquisition means acquiring the spectacle wearing parameter after manufacturing the spectacle of the spectacle wearer; and a comparison means making comparison between the spectacle wearing parameters acquired by the first spectacle wearing parameter acquisition means and the second spectacle wearing parameter acquisition means using figures, so that a spectacle wearing state can be compared and verified objectively and appropriately with the figure obtained by the comparison means.

According to the invention described in Claim 9 or Claim 10, a spectacle wearing test system includes: a spectacle wearing parameter measurement apparatus measuring a spectacle wearing parameter required to manufacture a spectacle suited to a spectacle wearer; a first spectacle wearing parameter acquisition means acquiring the spectacle wearing parameter before manufacturing the spectacle of the spectacle wearer; a second spectacle wearing parameter acquisition means acquiring the spectacle wearing parameter after manufacturing the spectacle of the spectacle wearer; a comparison means making comparison between the spectacle wearing parameters acquired by the first spectacle wearing parameter acquisition means and the second spectacle wearing parameter acquisition means using figures; and a verification means verifying by determining whether or not a spectacle wearing state is appropriate based on a figure obtained by the comparison means, so that a spectacle wearing state can be verified speedy and adequately with the verification means.

According to the invention described in Claim 11, a spectacle wearing test system includes: a spectacle wearing parameter measurement apparatus measuring a spectacle wearing parameter required to manufacture a spectacle suitable for a spectacle wearer; a memory means connected to the spectacle wearing parameter measurement apparatus in an information exchangeable manner and capable of recording, at least, a spectacle wearing parameter; a spectacle wearing parameter acquisition means acquiring the spectacle wearing parameter from the memory means; and a comparison means comparing the spectacle wearing parameter at present time measured by the spectacle wearing parameter measurement apparatus with the spectacle wearing parameter of the same spectacle wearer acquired by the spectacle wearing parameter acquisition means with figures, so that a spectacle wearing state at the present time can be compared and verified objectively and appropriately with the figure obtained by the comparison means.

According to the invention described in Claim 12 or Claim 13, a vision fixing means sets the spectacle wearer wearing a spectacle frame to be in a distance vision state or a near vision state and, in the near vision state, at least, one of an eyeball rotation angle and a near vision target distance can be changed optionally, an image input means takes an image of the spectacle wearer set in the distance vision state or the near vision state by the vision fixing means using an image pickup device to import the image; and a measurement and calculation means measure and calculate the spectacle wearing parameter based on the taken image obtained by the image input means, so that the spectacle wearing parameters in the distance vision state and near vision state can be measured with high accuracy. As a result, based on these spectacle wearing parameters with high accuracy, an optimal and dedicated spectacle lens for the spectacle wear can be designed and manufactured.

Further, the spectacle wearing parameter can be measured in the distance vision state and near vision state caused by the vision fixing means, respectively, allowing a selection of a required spectacle wearing parameter depending on a spectacle lens type of the spectacle worn by the spectacle wearer, so that a measurement speed can be improved by omitting to measure an unnecessary spectacle wearing parameter.

According to the invention described in Claim 14, a vision fixing means lets an eye of the spectacle wearer move in a rotating manner around a center of rotation of an eyeball together with an image pickup device to set the spectacle wearer in a distance vision state or near vision state, so that, even in the near vision state, the image pickup means can take an image of the spectacle wearer appropriately as in a case of the distance vision state, so that a spectacle wearing parameter can be measured with high accuracy.

According to the invention described in Claim 15, an eyeball rotation angle and a near vision target distance of spectacle wearing parameters are measured by being changed and determined by a vision fixing means while letting a spectacle wearer confirm an appropriate near vision state, so that an optimal eyeball rotation angle and near vision target distance for the spectacle wearer can be measured.

According to the invention described in Claim 16, a distance vision spectacle wearing distance and a near vision spectacle wearing distance are measured by a calculation in consideration of a three dimensional shape of a spectacle frame, so that these distance vision spectacle wearing distance and near vision spectacle wearing distance can be measured with high accuracy in that the respective measured distances are adjusted based on the three dimensional shape.

According to the invention described in Claim 17, a near vision inter-pupil distance is calculated on a spectacle lens surface of a spectacle worn by a spectacle wearer, so that the near vision inter-pupil distance required to manufacture the spectacle can be measured as an optimal value.

According to the invention described in Claim 18, a vision fixing beam in a distance vision state set by a vision fixing means is formed as a virtual image, so that a spectacle wearing parameter measurement apparatus can be downsized as compared to a case where the vision fixing beam in the distance vision state is formed as a real image.

According to the invention described in Claim 19, a measurement and calculation means detects blinking of a spectacle wearer and takes an image of the spectacle wearer when the spectacle wearer gazes unblinkingly, so that an image pickup failure of a face of the spectacle wearer can be reduced and thereby shortens measurement time of a spectacle wearing parameter by a spectacle wearing parameter measurement apparatus.

According to the invention described in Claim 20, a spectacle lens is manufactured using a spectacle wearing parameter measured by a spectacle wearing parameter measurement apparatus with high accuracy, so that the spectacle lens is enabled to be an optimal and dedicated spectacle lens for the spectacle wearer being a test subject of the spectacle wearing parameter.

According to the invention described in Claim 21, a spectacle wearing parameter is measured with high accuracy by a spectacle wearing parameter measurement apparatus, so that a spectacle manufactured based on the spectacle wearing parameter can be an optimal and dedicated spectacle for the spectacle wearer being a test subject of the spectacle wearing parameter.

BRIEF DESCRIPTION OF DRAWINGS

FIGS. 6(A) and 6(B) are side views showing states in which the measurement apparatus body takes an image of a spectacle wearer, in which FIGS. 6(A) shows the image pickup state at a measurement position in a distance vision state and 6(B) shows the image pickup state at a measurement position in a near vision state;

FIG. 9 is a view showing a structure of a measurement program stored in a device control terminal in FIG. 1;

FIG. 10 is a view showing an example data input screen for inputting data of a spectacle wearer;

FIG. 16(A) is an explanation view when measuring a distance vision inter-pupil distance in the measurement screen in FIG. 15, FIG. 16(B) is a graph showing a change in a reflected light amount on both pupils in FIG. 16(A), and FIG. 16(C) is an explanation view showing a comparison screen for comparing the distance vision inter-pupil distances before and after a spectacle manufacture;

FIG. 18(A) is a view showing an example measurement screen illustrating a side face image of the spectacle wearer in the distance vision state, and FIG. 18(B) is an explanation view illustrating a comparison screen for comparing the distance vision snectacle wearing distances and distance vision snectacle frame wearing angles before and after the spectacle fabrication, respectively;

FIG. 19 is a view showing an example save screen of spectacle wearing parameters;

FIG. 20 is a flowchart showing a measurement procedure, a comparative verification procedure, and the like;

FIG. 25 is views showing, as an example, parts of contents in a customer database in FIG. 1.

BEST MODE FOR CARRYING OUT THE INVENTION

Hereinafter, a best mode to implement the present invention will be described based on drawings.

Figure 1:
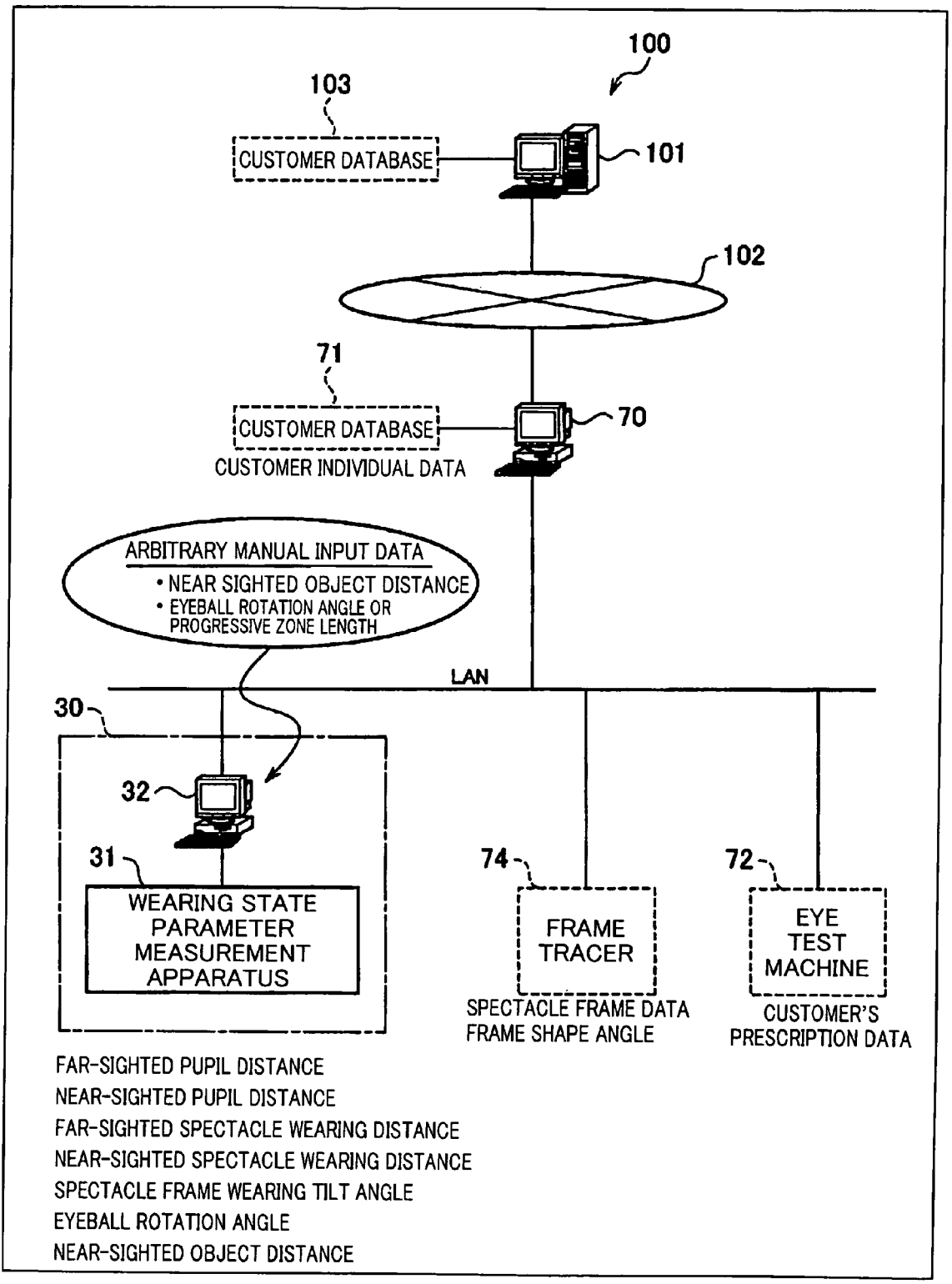
FIG. 1 is a communication circuit diagram showing an embodiment of a spectacle lens supply system, a spectacle wearing parameter measurement apparatus, and a spectacle wearing test system according to the present invention.

FIG. 1 is a communication circuit diagram showing an embodiment of a spectacle lens supply system, a spectacle wearing parameter measurement apparatus, and a spectacle wearing test system according to the present invention. As shown in FIG. 1, a spectacle lens supply system 100 is composed of a spectacle store terminal 70 serving as an order-placement side computer set at a spectacle store, an eye clinic, an individual, or so forth; a factory server 101 serving as a manufacturing side computer set at a spectacle lens manufacturing side such as a factory of a spectacle lens manufacturer; and a spectacle wearing parameter measurement apparatus 30 measuring a spectacle wearing parameter of a spectacle wearer and connected to the spectacle store terminal 70.

It is structured such that the spectacle store terminal 70 and the factory server 101 are connected to each other in an information exchangeable manner to each other via a public network 102 such as an Internet, and the spectacle store terminal 70 and the factory server 101 execute a process required to receive or place an order for a spectacle lens or a spectacle by exchanging data required to manufacture the spectacle. The spectacle store terminal 70 includes a customer database 71 serving as a memory and is capable of exchanging data required to manufacture the spectacle with the customer database 71. Meanwhile, the factory server 101 includes a customer database 103 serving as a memory and is capable of exchanging data required to manufacture the spectacle with the customer database 103.

The present embodiment has an embodiment in which the customer database exists at both the spectacle store side and the factory side, respectively, however, the customer database may exist at either the spectacle store side or the factory side.

Further, the customer database 71 at the spectacle store side may be built in the spectacle wearing parameter measurement apparatus 30, or the customer database 71 and the spectacle store terminal 70 may be built in the spectacle wearing parameter measurement apparatus 30 as an embodiment. At that time, the spectacle wearing test system may be composed of the apparatus, in which the customer database 71, or the customer database 71 and spectacle store terminal 70 is/are built, alone.

As a memory of the customer database 71 at the spectacle store side or the customer database 103 at the factory side, for example, there are a hard disk, a CD-ROM, and so forth.

Here, the above-described data required to manufacture the spectacle is, at least, one of a customer personal data X, a spectacle lens data W, a spectacle prescription data Y, a spectacle frame data Z, a spectacle wearing parameter V, a processing instruction data (not shown), as shown in FIG. 25, and is/are prepared for each spectacle wearer to be recorded and stored in the customer database 71 and/or the customer database 103 in a displayable form, for example, in a display screen.

The customer personal data X includes an ID number, gender, name, telephone number, address, birthday, age, profession, interest, ordered laboratory, order-placement date, order receiver, order receiver address, order receiver telephone number, and so forth, which are related to the customer, as shown in FIG. 25(A). FIG. 25(B) is a "first-registration prescription" indicating a prescription detail for a specific customer shown in the customer personal data X (namely, a spectacle wearer) at the time when the customer places the order first. In this "first entry prescription", the spectacle lens data W, spectacle prescription data Y, spectacle frame data Z, spectacle wearing parameter V, processing instruction data, and the like are indicated in addition to a type being a presbyopia, myopia, or astigmatism, a medical condition (chief complaint), intended purpose, number of order(s) placed, and the like are displayed in a table.

The spectacle lens data W includes a product name of the spectacle lens, lens material, refractive index, coating, and so forth. Further, the spectacle prescription data Y includes a spherical diopter of the spectacle lens "SPH" (unit: dpt), an astigmatic diopter "CYL" (unit: dpt), a cylinder axis "AXS" (unit: °), an addition (unit: dpt), x-direction prism diopter "PX" (unit: Δdpt), y-direction prism diopter "PY" (unit: Δdpt), and so forth. Further, the spectacle frame data includes a frame number of a spectacle frame, spectacle frame name, frame material, frame color and shape, and so forth. Note that "L" and "R" in FIG. 25(B) indicate a left eye and right eye, respectively.

The processing instruction data represents a processing instruction to set a spectacle lens thickness to be a requisite minimum value, an instruction to chamfer so as to obscure the frame thickness of the spectacle lens, or so forth. Further, the spectacle wearing parameter V, which will be described later in the description of the spectacle wearing parameter measurement apparatus 30, is, at least, one of a distance vision inter-pupil distance "FPD" (unit: mm), a near vision inter-pupil distance "NPD" (unit: mm), a distance vision spectacle wearing distance "FVD" (unit: mm, the same as a later-described "A"), a near vision spectacle wearing distance "NVD" (unit: mm, the same as a later-described "B"), a spectacle frame-wearing angle "ST" (unit: °, the same as a later-described "a"), an eyeball rotation angle "RA" (unit: °, the same as a later-described "θ"), and a near vision target distance "ODS" (unit: mm, the same as a later-described "NL"). When the same customer (namely, the spectacle wearer) places the second order, a "second registration prescription" is prepared as in the same manner as of the "first-registration prescription" to be recorded and stored in the customer database 71 and/or the customer database 103.

The spectacle store terminal 70 exchanges the personal data of the spectacle wearer required to manufacture the spectacle with the factory server 101, as described above. In other words, by following a guide screen on a monitor, the spectacle store terminal 70 transmits the personal data of the spectacle wearer required to manufacture the spectacle, and at the same time; transmits an order type designation out of an unprocessed spectacle lens, a processed spectacle lens of which peripheral edge is shaped into a spectacle frame shape, and a spectacle lens already set in the spectacle frame; receives data of an expected finished shape of the spectacle lens or the like supplied from the factory server 101; and implements the order processing. The above-described expected finished shape of the spectacle lens or the like is to be calculated by the factory server 101 based on the spectacle wearer's personal data, which is required to manufacture the spectacle lens and received from the spectacle store terminal 70, to be sent to the spectacle store terminal 70 for confirmation.

The factory server 101 is connected to the spectacle store terminal 70 via the public network 102 as described above, and at the same time, connected to a not-shown processing device and measurement apparatus in the factory. Then, the factory server 101 calculates the expected finished shape of the spectacle lens or the like using the spectacle wearer's personal data required to manufacture the spectacle, which is received from the spectacle store terminal 70, and at the same time, serves to manufacture the spectacle by transmitting the data to the processing and measurement devices to thereby let the processing device manufacture the spectacle lens or the spectacle in accordance with the order type to provide the spectacle lens or the spectacle to the spectacle wearer.

The factory server 101 manages the spectacle wearer's personal data required to manufacture the spectacle, which is received from the spectacle store terminal 70, the expected finished shape data of the spectacle lens or the like, and the processing data by recording and storing them into the customer database 103. The factory server 101 is further configured to be information exchangeable with respective systems related to the order receipt and placement of the spectacle lens or the like such as a not-shown inventory control system, accounting control system, order system, or the like by being connected to the respective systems.

The factory server 101 further includes an input/output unit, an arithmetic and control unit, a database unit, and the like. The input/output unit is provided with, for example, an input means composed of a keyboard, a mouse, a floppy (registered trademark) disk (FD), a CR-R, or the like; and an output means composed of a display, a printer, or the like. Further, in the database unit, the customer database 103, a lens design table (lens data table), a lens processing table, and the like are stored.

The arithmetic and control unit is composed of a CPU, a ROM, a RAM with a lens design program, an optical performance evaluation program, a lens processing program, a special control program, and the like installed in addition to a general control program provided in a general computer.

The lens design program includes an optical design program calculating curves of the concave and convex surfaces of the lens and the lens thickness by accessing the database unit; a lens weight calculation program; and other program(s) required for the lens design. Further, the optical performance evaluation program includes a program evaluating the optical performance of the lens by obtaining an astigmatism, a curvature of field, a distortion, and the like. When the optical performance does not satisfy a predetermined performance, goes back to the lens design program to redesign, and when the optical performance satisfies a predetermined performance, then goes to the next step.

The lens processing program includes: a program generating a processing data by combining data required to process the spectacle lens such as a lens refractive surface shape, a lens edge shape, a bevel edging shape, and the like. Further, the special control program includes a customer data read/write program to execute a read, check, record (includes a temporary recording), write, update, and new addition of the data by accessing the customer database 103 or the like; a data check program; a graphic display program such as a lens shape or a lens thickness comparison table; or so forth.

The spectacle wearing parameter measurement apparatus 30 is an apparatus to measure the spectacle wearing parameter for manufacturing the spectacle suited to the spectacle wearer, and, as will be described later, includes a device control terminal 32 including a measurement program. The device control terminal 32 exchanges the personal data information of the spectacle wearer required to manufacture the spectacle including the spectacle wearing parameter, via the spectacle store terminal 70 with the customer database 71; and further exchanges the data with the customer database 103 via the spectacle store terminal 70 and the factory server 101 to import the data from the customer database 71 or the customer database 103, or record and store in the customer database 71 and/or the customer database 103. Further, the spectacle wearing parameter measurement apparatus 30 is configured to include a measurement apparatus body 31 and the device control terminal 32.

Figure 2:
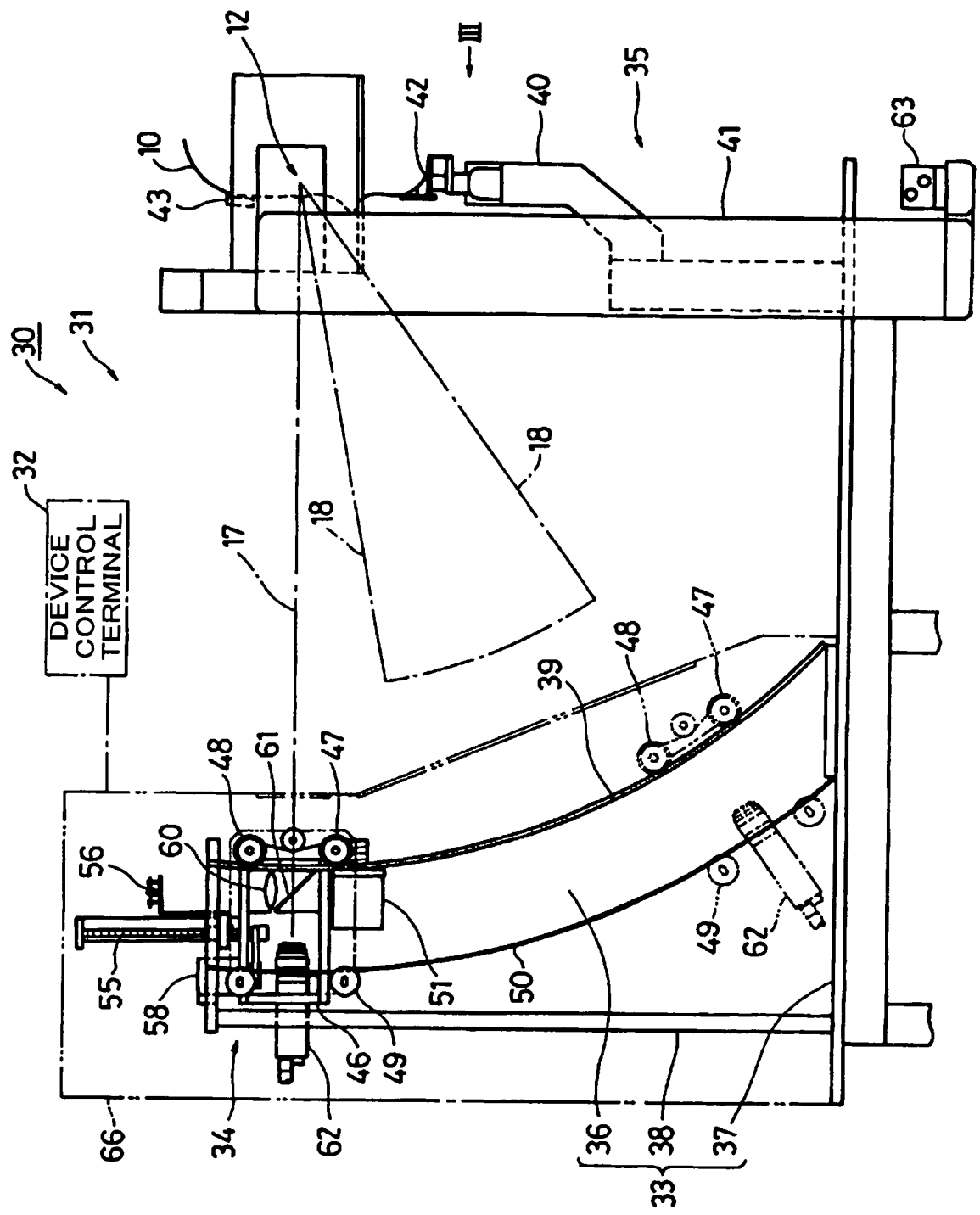
FIG. 2 is a side view showing part of the spectacle wearing parameter measurement apparatus in FIG. 1.
Figure 3:
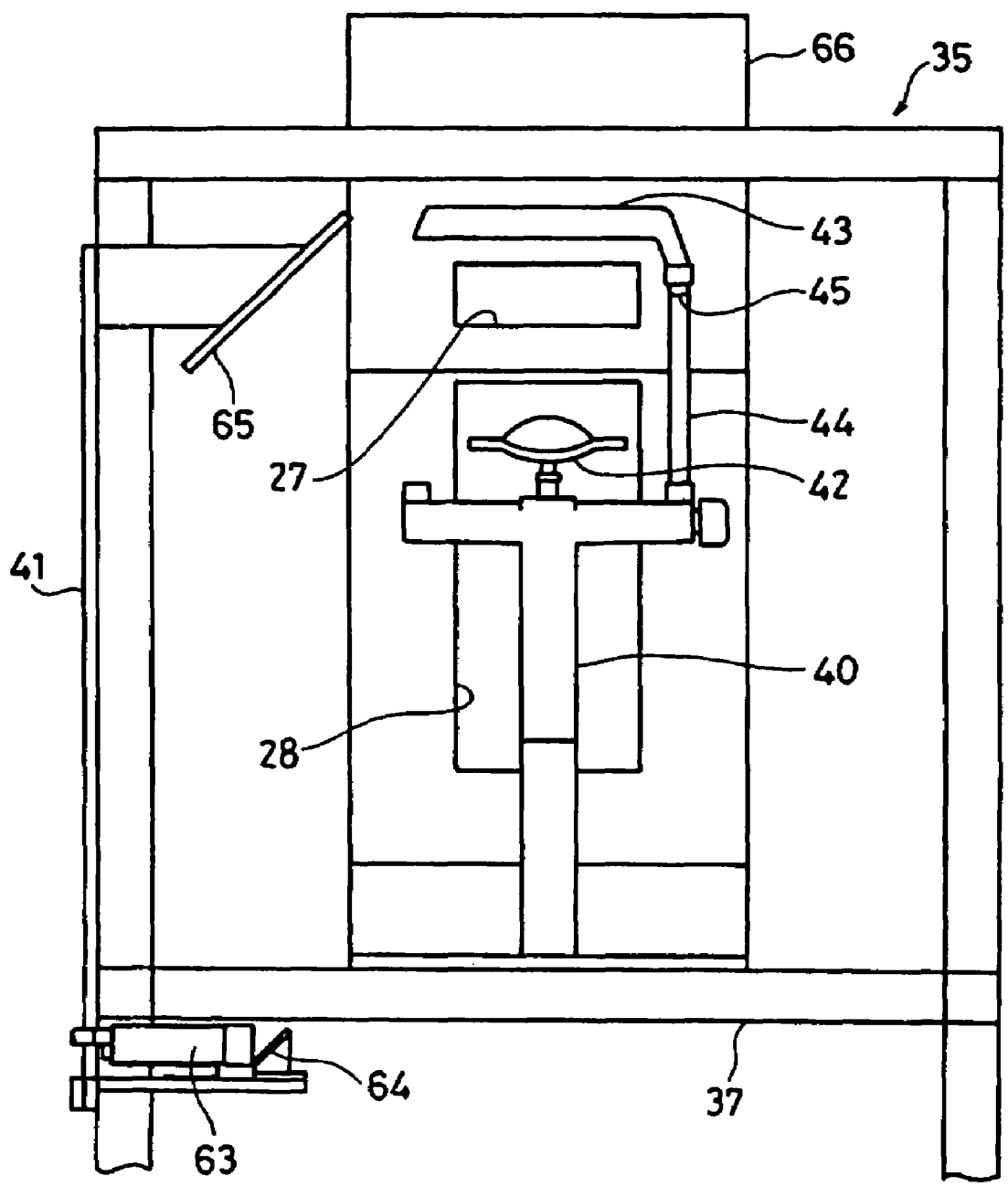
FIG. 3 is a view from an arrow direction in FIG. 2.

FIG. 2 is a side view showing the spectacle wearing parameter measurement apparatus in FIG. 1 by breaking it partly. FIG. 3 is a view viewing from an arrow direction in FIG. 2.

Here, the spectacle wearing parameter is, at least, one of the distance vision inter-pupil distance, the near vision inter-pupil distance, the distance vision spectacle wearing distance, the near vision spectacle wearing distance B spectacle frame-wearing angle, an eyeball rotation angle and the near vision target distance. A description will be given of these spectacle wearing parameters below using FIG. 21 to FIG. 23.

Figure 21:
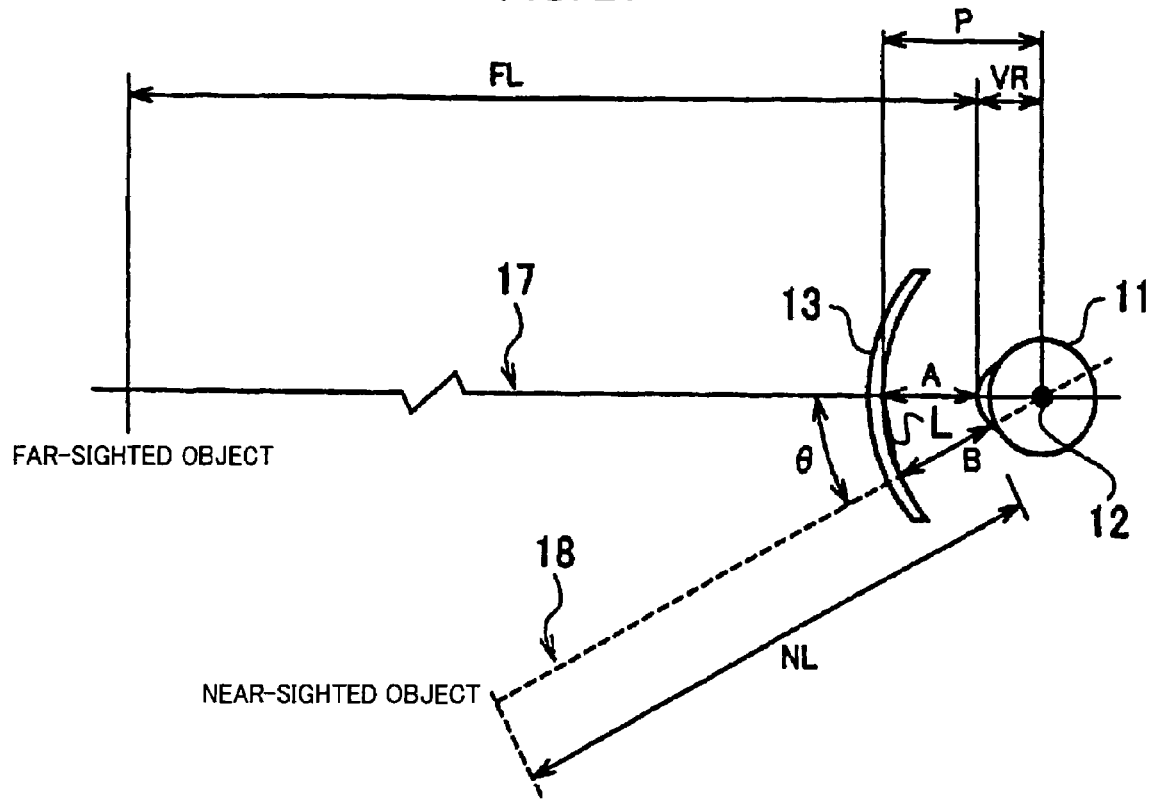
FIG. 21 is an explanation view for explaining the distance vision spectacle wearing distance, the near vision spectacle wearing distance, an eye rotation angle, a near vision target distance, and so on, out of the spectacle wearing parameters.
Figure 22:
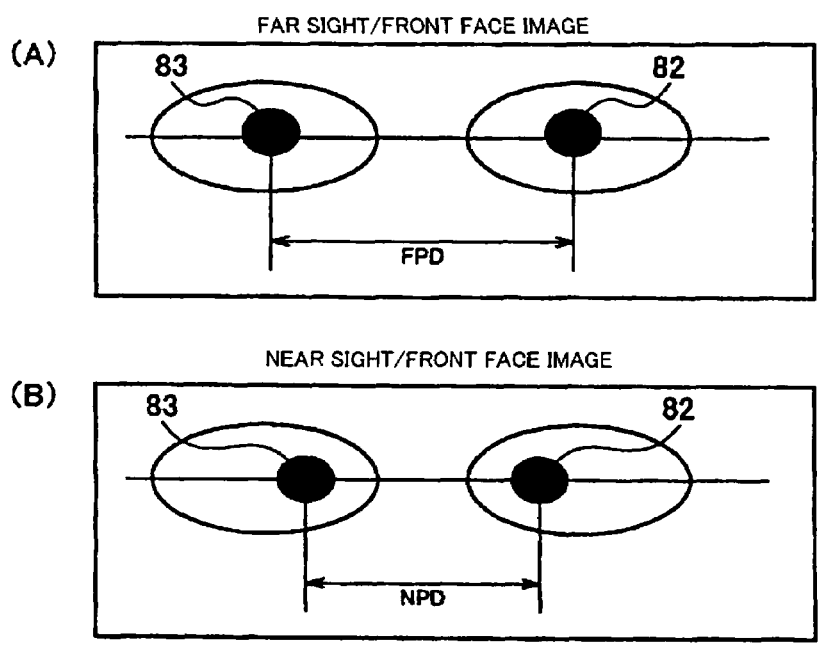
FIGS. 22(A) and 22(B) are explanation views for explaining the distance vision inter-pupil distance and the near vision inter-pupil distance, respectively.

The distance vision inter-pupil distance is an inter-pupil distance between a left eye 82 and a right eye 83 gazing the distance being 5 m or more distant therefrom, and is denoted by FPD of a distance vision front image in FIG. 22. The near vision inter-pupil distance is the inter-pupil distance between the left eye 82 and the right eye 83 gazing a target at a near vision target distance (generally, approximately 30 cm to 50 cm) therefrom, and is denoted by NPD of the distance vision front image in FIG. 22. The distance vision spectacle wearing distance (distance between vertexes) is a distance from a rear surface of a spectacle lens 13 on a distance vision axis 17 of the spectacle wearer to a corneal vertex of an eyeball (test subject eye 11) in FIG. 21 and denoted by "A" in the drawing. The near vision spectacle wearing distance is a distance from the rear surface of the spectacle lens 13 on a near vision axis 18 of the spectacle wearer to the corneal vertex of the eyeball (test subject eye 11) in FIG. 21, and denoted by "B" in the drawing. A VR in the drawing denotes a distance from the corneal vertex of the test subject eye 11 to a center of rotation 12 of the eyeball.

Generally, in a near vision state (for example in reading), a test subject being a spectacle wearer rotates the test subject eye 11 around the center of eye 12 of an eyeball (test subject eye 11) and observes a near vision target by lowering a sight line. The eyeball rotation angle $\theta$ is an angle formed between both the vision axes 17, 18 when the sight line is lowered from the distance vision axis 17 to the near vision axis 18. The near vision target distance is a distance from the eye (test subject eye 11) to the near vision target when observing the near vision target in the near vision state and denoted by "NL" in the drawing. Note that "FL" in the drawing denotes a distance from the eye (test subject eye 11) observing the distance vision target in the distance vision state to the distance vision target.

Figure 23:
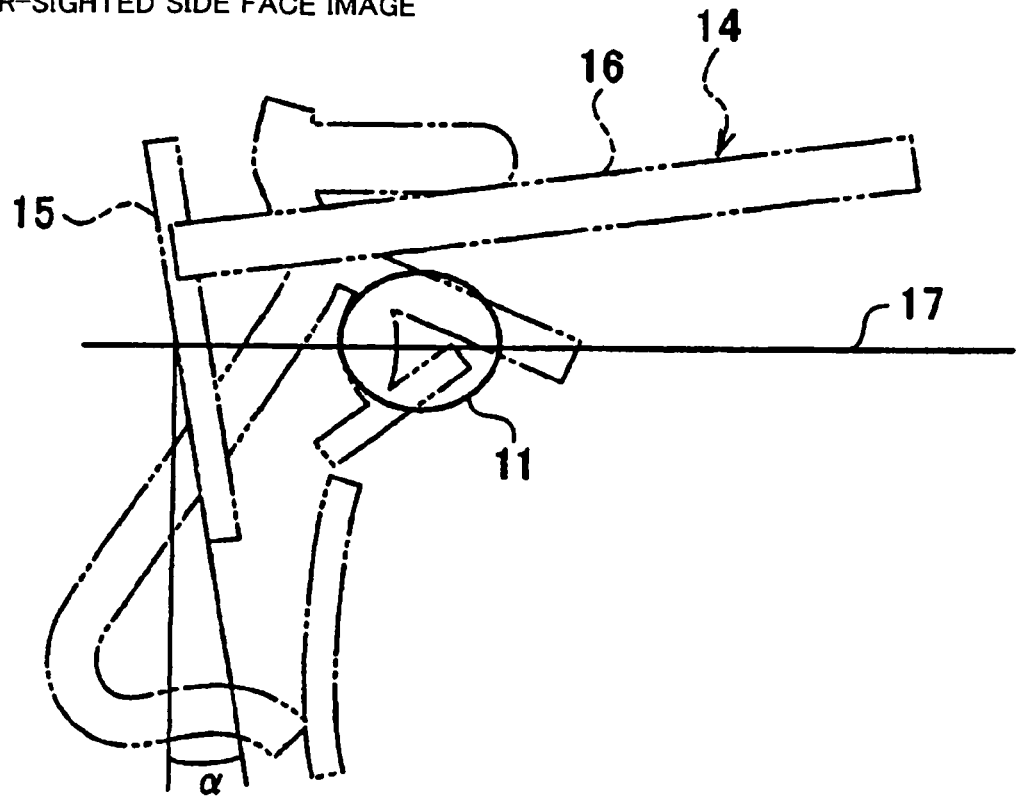
FIG. 23 is an explanation view for explaining the spectacle frame wearing angle out of the spectacle wearing parameters.
Figure 24:
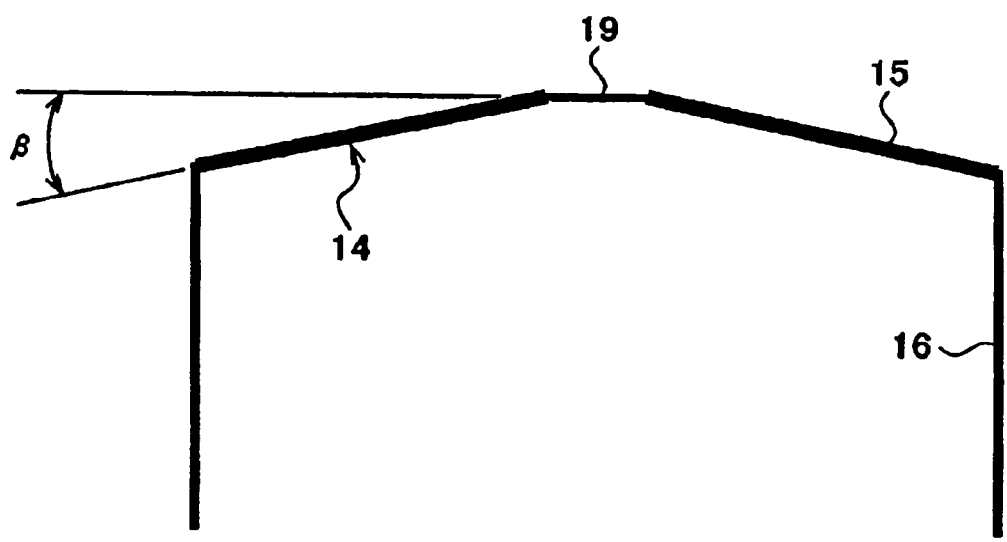
FIG. 24 is an explanation view for explaining a frame horizontal tilt angle.

As shown in FIG. 23, an angle formed by a temple 16 and a rim 15 of a spectacle frame 14 is commonly called a frame tilt angle, however, in the present embodiment, the spectacle frame wearing angle indicates an angle a formed by the edge formed by the rim 15 of a spectacle frame 14 and an optical axis being defined as the distance vision axis 17 of the spectacle wearer in the distance vision state. Further, a horizontal frame tilt angle differs depending on the respective frames 14, and indicates an angle $\beta$ of the edge in FIG. 24, which is formed by the rim 15 when viewing the spectacle frame 14 from the top, with respect to a bridge 19.

Meanwhile, the measurement apparatus body 31 is, as shown in FIG. 2, configured to include a frame unit 33 provided with a pair of orbital frames 36 of a curved shape, a movable unit 34 moving on the orbital frames 36, and a positioning unit 35 positioning a face of a test subject 10 being a spectacle wearer.

In the frame unit 33, a column frame 38 is provided to stand on a base 37, and the orbital frames 36 stand on the base 37 to rest on the column frame 38 to be supported thereby. On the orbital planes of the respective orbital frames 36, a rack rail 39 is provided, respectively.

On the above-described base 37, as shown in FIG. 3, a positioning main frame 40 and a positioning sub frame 41 of the positioning unit 35 are provided to stand. On the top of the positioning main frame 40, there are provided a chin rest 42, on which a chin of the test subject 10 is placed, and a forehead support 43 to which a forehead of the test subject 10 is fitted. The forehead support 43 is supported by the chin rest 42 via a forehead support column 44 on which a reference mark 45 to position the height of the eye of the test subject 10 is provided.

Figure 4:
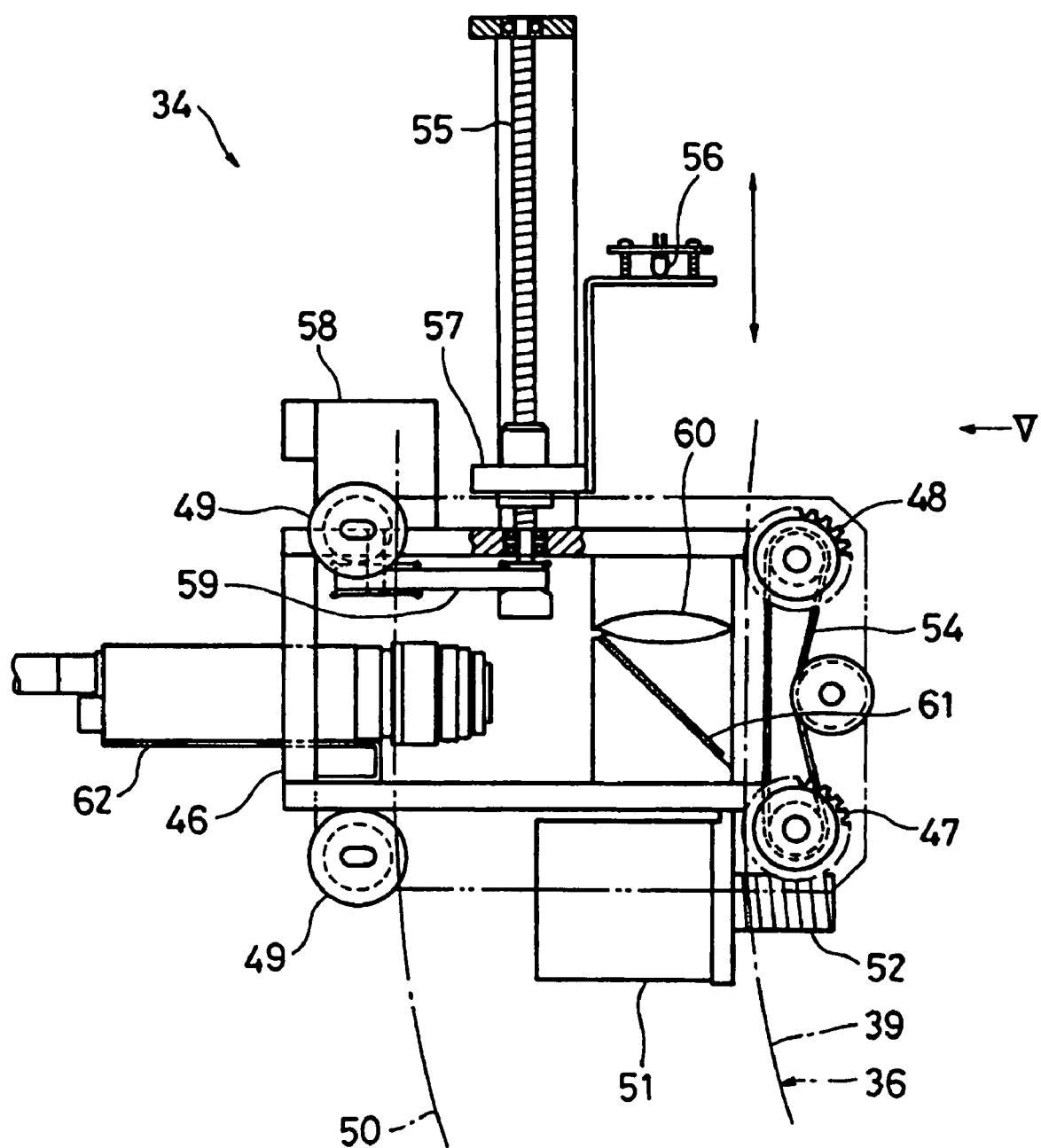
FIG. 4 is a side view showing a movable unit in FIG. 2.
Figure 5:
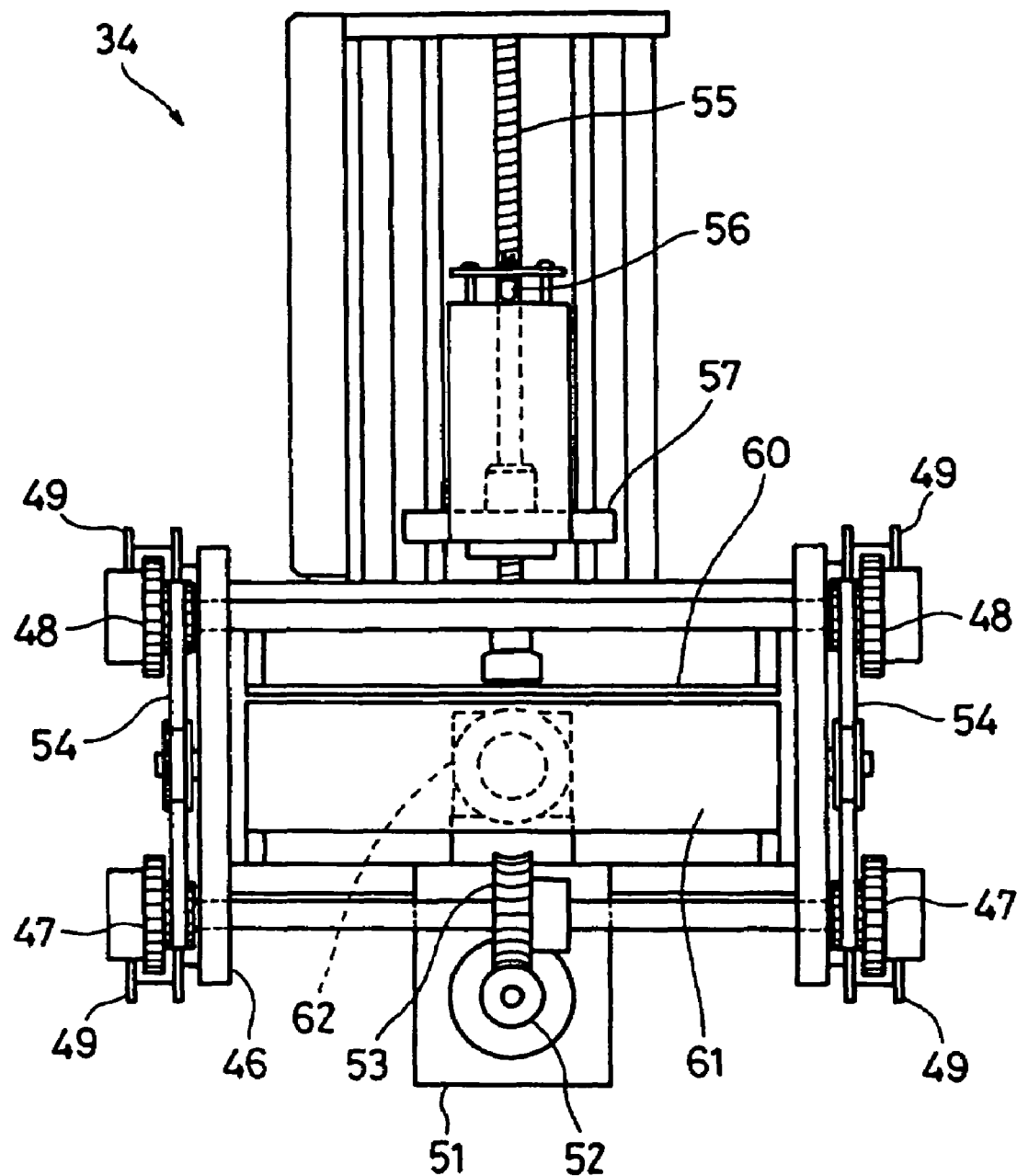
FIG. 5 is a view from an arrow direction in FIG. 4.

Meanwhile, as shown in FIG. 4 and FIG. 5, a pair of driving gears 47, which can rotate synchronously, are disposed in a freely rotatable manner at a unit frame 46 of the above-described movable unit 34, and, similarly, a pair of driving gears 48 are disposed in a freely rotatable manner above the pair of driving gears 47 in the drawing. These driving gears 47 and driving gears 48 engage with the rack rails 39 of the orbital frames 36. Further, at the unit frame 46, guide rollers 49 are pivotally supported in a rotatable manner on an opposite side of the driving gears 47 and driving gears 48, and these guide rollers 49 are fitted to back surface portions 50 of the orbital frames 36.

Further, a motor for rotation 51 is provided at the unit frame 46, and a worm 52 is mounted to a motor shaft of the motor for rotation 51 integrally in a rotatable manner. The worm 52 engages with a worm wheel 53 provided at a shaft coupling the pair of driving gears 47 and a driving force of the motor for rotation 51 is transmitted to the driving gears 47 via the worm 52 and the worm wheel 53 to further the driving gears 48 via a timing belt 54. The driving gears 47 and driving gears 48 engage with the rack rails of the orbital frames 36 and rotate by being driven by the motor for rotation 51, and at this time, the guide rollers 49 moves on the back surface portions 50 of the orbital frames 36 in a rotating manner, then the movable unit 34 moves along the curved shape of the orbital frames 36 in a rotating manner. As shown in FIG. 2, the center of the rotating movement of the movable unit 34 is designed to be the center of rotation 12 of the eyeball of the test subject 10 positioned by the positioning unit 35.

As shown in FIG. 4 and FIG. 5, a driving screw 55 is provided to stand at the unit frame 46 of the movable unit 34 in a freely rotatable manner around the shaft thereof. A light source supporting portion 57 supporting a light source 56 such as a light-emitting diode (LED) is screwed together with the driving screw 55. A motor for light source 58 is set at the unit frame 46, and the driving force of the motor for light source 58 is transmitted to the driving screw 55 via a timing belt 59 to rotate the driving screw 55. Because of this, the light source 56 is provided in an approaching or leaving direction to/from a later-described lens 60 in a movable manner via the light source supporting portion 57.

The lens 60 is disposed in the unit frame 46 of the movable unit 34, and the light source 56 is disposed on the optical axis of the lens 60. The movable unit 34 having these lens 60 and light source 56 composes a vision fixing means setting the spectacle wearer wearing the spectacle frame at respective measurement positions for the distance vision state and near vision state. The setting of the measurement positions of these distance vision state and near vision state is realized by moving the light source 56 to approach or leave to/from the lens 60 and, at the same time, by moving the movable unit 34 along the curved shape of the orbital frames 36 in a rotating manner.

In other words, as shown in FIG. 6, the distance between the light source 56 and the lens 60 is arbitrarily set to thereby let the test subject 10 being a spectacle wearer observe images of the light source 56 in the distance vision state and the near vision state as vision fixing beams (distance vision target and near vision target). At the same time, by moving the movable unit 34 along the curved shape of the orbital frames 36, at the measurement position in the distance vision state (FIG. 6(A)), the image of the light source 56 is generated on the distance vision axis 17 in the substantially horizontal direction of the test subject eye 11 of the test subject 10, while, at the measurement position in the near vision state (FIG. 6(B)), the image of the light source 56 is generated on the near vision axis 18, which is rotated at an angle of θ degrees downward with respect to the distance vision axis 17 of the test subject eye 11 of the test subject 10. Based on these, the setting of the respective measurement positions in the distance vision state and near vision state is realized.

In particular, at the near vision-state measurement position shown in FIG. 6(B), because of the rotational movement of the movable unit 34 along the curved shape of the orbital frames 36, the eyeball rotation angle θ can be changed arbitrarily, and further, the adjustment of the distance between the light source 56 and the lens 60 allows the near vision target distance NL to be changed arbitrarily. Note that these eyeball rotation angle θ and near vision target distance NL can be structured such that one of them can be changed. Further, the light source 56 is used together for both the distance vision and near vision purposes by being approached or left to/from the lens 60, however, it is also possible to provide the light sources separately for the distance vision and the near vision.

As shown in FIG. 4 and FIG. 5, a half mirror 61 serving as a beam splitter is arranged below the lens 60 in a drawing in the unit frame 46 of the movable unit 34. The half mirror 61 is arranged at an angle of 45° to reflect and direct the light emitted from the light source 56 to the positioning unit 35 side. In the unit frame 46, as a photographic device, a front image-pickup camera 62 is set rearward of the half mirror 61. The front image-pickup camera 62 is, for example, a CCD camera or the like with an image pickup lens.

As shown in FIG. 2, when the movable unit 34 moves along the curved shape of the orbital frames 36 in a rotating manner around the center of rotation 12 of the eyeball of the test subject 10 (test subject eye 11), the movable unit 34 similarly moves the front image-pickup camera 62 set in the movable unit 34 in a rotating manner. At that time, as shown in FIG. 6, the optical axis of the front image-pickup camera 62 is always kept to be in a state matching with the distance vision axis 17 or the near vision axis 18 of the test subject 10. Accordingly, the front image-pickup camera 62 takes and imports, through the half mirror 61, an image of the front face of the test subject 10 set at the respective measurement positions for the distance vision state or the near vision state by the movable unit 34. Note that, for the ratio of transmittance and reflectance of the half mirror 61, 7:3 is applied here, whereas the ratio is not specifically determined. Further, the distance between the half mirror 61 and the eye of the test subject 10, of which position is determined by the positioning unit 35, is set to be approximately 70 cm.

As shown in FIG. 2 and FIG. 3, at the positioning sub frame 41 of the positioning unit 35, a side image-pickup camera 63, a mirror 64 and a mirror 65 are set. The side image-pickup camera 63 is set left downward of the chin rest 42 in FIG. 3 and is, for example, a CCD camera with the image pickup lens. The mirror 64 is set in the vicinity of the side image-pickup camera 63 and the mirror 65 is set in the vicinity of the forehead support 43, respectively, tilted at an angle of 45°. The side face of the test subject 10 set at the respective measurement positions for the distance vision state and the near vision state by the movable unit 34 is reflected by the mirror 64 and mirror 65 sequentially to thereby be taken by the side image-pickup camera 63 and the image is imported. The front image-pickup camera 62, the half mirror 61, the side image-pickup camera 63, the mirror 64 and the mirror 65 serve as an image taking and importing means.

Figure 8:
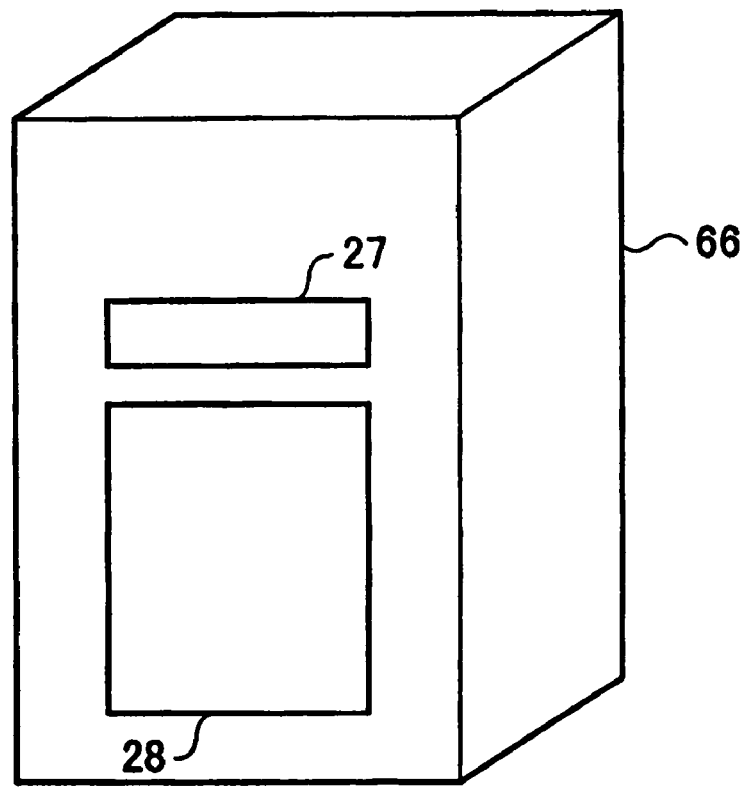
FIG. 8 is a perspective view showing a cover in FIG. 2 and FIG. 3.

As shown in FIG. 2, the movable unit 34 having the frame unit 33 provided with the orbital frames 36, the light source 56, the lens 60, the half mirror 61, the front image-pickup camera 62 and the like is covered by a cover 66. As shown in FIG. 3 and FIG. 8, the cover 66 has openings, namely a distance vision window 27 and a near vision window 28 on the front surface side. As shown in FIG. 2, the distance vision window 27 is formed at a position which the distance vision axis 17 of the test subject eye 11 crosses the cover 66 when the test subject 10 whose face position is determined by the positioning unit 35 is in the distance vision state. Similarly, the near vision window 28 is formed at a position, which the near vision axis 18 of the test subject eye 11 crosses the cover 66 when the test subject 10 whose face position is determined by the positioning unit 35 is in the near vision state, and in an area in which the near vision axis 18 moves in a rotating manner by a change in the eyeball rotation angle θ.

The previously-described device control terminal 32, which is shown in FIG. 1 and stores measurement program software shown in FIG. 9, activates a vision fixing beam driving program software capable of setting the distance vision state or the near vision state, moves the movable unit 34 in a rotating manner by driving and controlling the motor for rotation 51, moves the light source 56 by driving and controlling the motor for light source 58, and, as will be described below, determines the eyeball rotation angle θ and the near vision target distance NL, out of the spectacle wearing parameters in the near vision state.

Further, by activating the measurement program software, the device control terminal 32 serves as a measurement and calculation means, which reads and displays the taken image taken by the front image-pickup camera 62 and the side image-pickup camera 63 and temporarily stored in the device control terminal 32 onto a monitor, and measures and calculate based on the taken image, out of the spectacle wearing parameters, the distance inter-pupil distance FPD, the near vision inter-pupil distance NPD, the distance vision spectacle wearing distance A, the near vision spectacle wearing distance B, and the spectacle frame wearing angle a. Further, a calibration program software, out of the measurement program softwares, serves to match the magnification of the image taken by the front image-pickup camera 62 and the side image-pickup camera 63 by correcting the image as described later.

Further, by activating a measurement-comparison-verification program software out of the measurement program softwares, the device control terminal 32 serves: as a measurement and calculation means determining by measuring and calculating, same as in the case of the above-described measurement program software, the distance vision inter-pupil distance FDP, the near vision inter-pupil distance NPD, the distance vision spectacle wearing distance A, the near vision spectacle wearing distance B, and the spectacle frame wearing angle a of the spectacle wearer at the time after manufacturing the spectacle; at the same time, as a comparison means importing the distance vision inter-pupil distance FDP, the near vision inter-pupil distance NPD, the distance vision spectacle wearing distance A, the near vision spectacle wearing distance B, and the spectacle frame wearing angle a, of the same spectacle wearer before manufacturing the spectacle, which are stored in the customer database 71 or the customer database 103, and comparing with a figure the imported respective spectacle wearing parameters with the spectacle parameters measured as described above; and further as a verification means determining and verifying whether or not the current spectacle wearing state is appropriate for the spectacle wearer.

The spectacle wearing test system is composed of, at least, one of the spectacle wearing parameter measurement apparatus 30 including the device control terminal 32 provided with these functions (measurement and calculation means, comparison means and verification means), the customer database 71 and the customer database 103.

Figure 20:
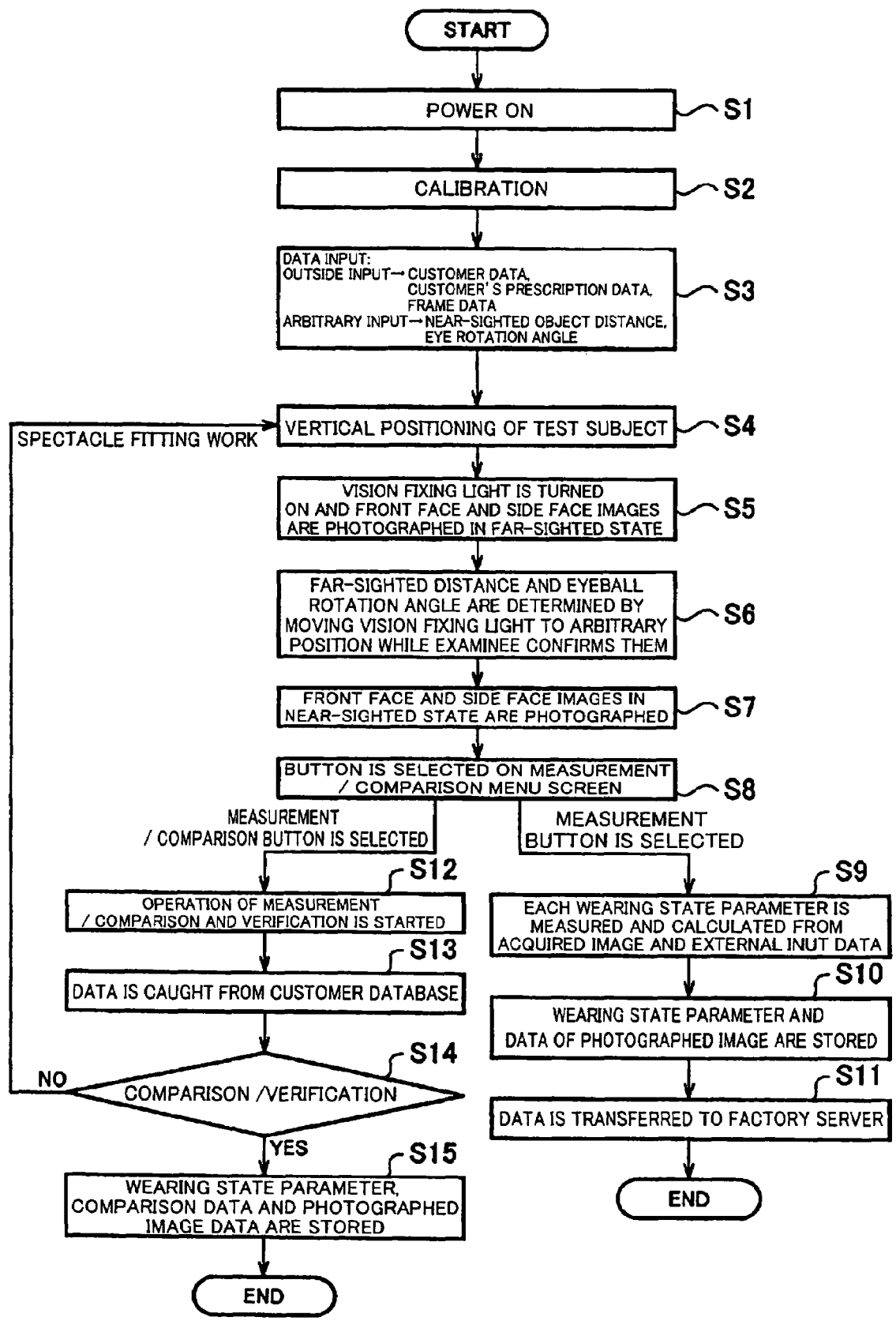

The measurement procedure, and the comparison and verification procedure executed by the device control terminal 32 will be outlined first with reference to a flowchart shown in FIG. 20 and the detailed description will be given thereafter.

First, on the spectacle wearing parameter measurement apparatus 30, a power is turned on to activate the device control terminal 32 (S1); and the calibration to correct the magnification of the image taken by the front image-pickup camera 62 and the side image-pickup camera 63 is executed as required (S2). Next, the customer personal data, the spectacle prescription data and the spectacle frame data are input from outside, and the near vision target distance NL and the eyeball rotation angle θ are arbitrarily inputted (S3).

After that, the eye of the test subject 10 being a spectacle wearer is adjusted to match with the reference mark 45 (FIG. 3) of the positioning unit 35 and a vertical positioning of the eye of the test subject 10 is performed (S4). In this state, the vision fixing beam is put on approximately five meters forward, and the images of the front and side faces of the test subject 10 in the distance vision state are taken (S5).

Next, with the vision fixing beam being put on, these near vision target distance NL and eyeball rotation angle θ are determined by arbitrarily changing the near vision target distance NL and the eyeball rotation angle θ while letting the test subject 10 confirm an appropriate near vision state (S6). In this state, the images of the front and side surfaces of the test subject 10 in the near vision state are taken (S7).

After the images are taken, a measurement and comparison menu screen (FIG. 12) is displayed on a monitor of the device control terminal 32. In the measurement and comparison menu screen, any one of a "measurement" button (namely, an inter-pupil distance measurement button 80 or a spectacle wearing angle and distance measurement button 81) and a "measurement and comparison" button (namely, an inter-pupil distance measurement and comparison button or a spectacle wearing angle and distance measurement and comparison button 91) is selectable (S8).

In the measurement and comparison menu screen, when the "measurement" button is selected, based on the taken images in the distance vision and near vision state and the data inputted from outside, the spectacle wearing parameters (the distance inter-pupil distance FPD, the near vision inter-pupil distance NPD, the distance vision spectacle wearing distance A, the near vision spectacle wearing distance B and the spectacle frame wearing angle a) are measured and calculated.

Then, these measured spectacle wearing parameters are stored in the device control terminal 32 together with the taken images, and thereby stored in the customer database 71 via the spectacle store terminal 70 (S10).

After the above-described operations S1 to S9 performed by the spectacle wearing parameter measurement apparatus 30, the spectacle store terminal 70 transmits (transfers) the personal data of each spectacle wearer (at least, one of the customer personal data X, the spectacle lens data W, the spectacle prescription data Y, the spectacle frame data Z, the spectacle wearing parameter V, and the processing instruction data), which is required to manufacture the spectacle and stored in the customer database 71, to the factory server 101 of the spectacle manufacturer to place the order for the spectacle lens or the spectacle (S11).

In the measurement and comparison menu screen in Step S8, when the "measurement and comparison" button is selected, a measurement, comparison, and verification operation to confirm the spectacle wearing state of the spectacle wearer wearing the manufactured spectacle is started (S12). At this time, the images of the spectacle wearer wearing the manufactured spectacle in the distance vision state and the near vision state are taken in Step S5 and S7. Accordingly, first, based on these images and the data inputted outside, as in Step S9, the spectacle wearing parameters are measured and calculated.

Next, the spectacle wearing parameters of the same spectacle wearer measured before manufacturing the spectacle to manufacture the spectacle are imported from the customer database 71 or the customer database 103 (S13). The comparison is made between the imported spectacle wearing parameters (the distance inter-pupil distance FPD, the near vision inter-pupil distance NPD, the distance vision spectacle wearing distance A, the near vision spectacle wearing distance B, and the spectacle frame wearing angle a, respectively) and the spectacle wearing parameters measured in Step S12 (the distance inter-pupil distance FPD, the near vision inter-pupil distance NPD, the distance vision spectacle wearing distance A, the near vision spectacle wearing distance B, and the spectacle frame wearing angle a, respectively), with figures, and determination and verification are performed (S14).

When the respective spectacle wearing parameters are within an allowable range in the comparison and verification in Step S14, the spectacle wearing parameters measured in Step S12 and the comparison data compared in Step S14 are stored in the customer database 71 and/or the customer database 103, together with the taken images of the spectacle wearer wearing the manufactured spectacle (S15). Further, in the comparison and verification in Step S14, when any of the spectacle wearing parameters is over the allowable range, the fitting of the spectacle frame 14 is adjusted, and the operations in Step S4 and thereafter (S4 to S8 and S12 to S14) are repeated.

[Activation (S1)]

In FIG. 1, when the measurement apparatus body 31 of the spectacle wearing parameter measurement apparatus 30 is powered on, the device control terminal 32 connected to the measurement apparatus body 31 is activated.

[Calibration (S2)]

Since the two image-pickup cameras 62, 63 taking the front face image and the side face image, respectively, may be different in magnification, a calibration button 67 is selected in a image pickup menu screen (FIG. 11) displayed on the monitor on the device control terminal 32 to thereby execute the calibration, as required. In the calibration, the difference between the front face image and the side face image due to a magnification difference is corrected based on the magnification difference, by previously obtaining the magnification difference between the image-pickup cameras 62, 63 using the images of scales or the like taken by both the image-pickup cameras 62, 63, respectively.

[Data Input (S3)]

Next, using a data input screen displayed on the monitor of the device control terminal 32, for example, a data input screen shown in FIG. 10, the customer personal data X, the spectacle prescription data Y, and the spectacle frame data Z are inputted. These data can be inputted by hand, whereas they can be read automatically from outside to eliminate such a trouble or an input error.

For instance, in FIG. 10, when the customer personal data X has already been inputted, only an input of the ID number allows an automatic input of the data by reading from the customer file of the customer database 71 (FIG. 1) via the spectacle store terminal 70. Further, the spectacle prescription data Y can be transferred only by an operation of a button 73 (FIG. 10) when the device control terminal 32 of the spectacle wearing parameter measurement apparatus 30 and an eye inspection apparatus 72 (a phoropter, an autorefractometer, or the like) are connectable. Also, the spectacle frame data Z including the frame horizontal tilt angle β can be transferred only by an operation of a button 75 (FIG. 10) when the device control terminal 32 of the spectacle wearing parameter measurement apparatus 30 and a frame tracer 74 (FIG. 1) are connectable. Thus, the frame horizontal tilt angle β is obtainable from trace data of the spectacle frame 14 measured by the frame tracer 74, however, as one of the other acquisition methods, for example, it is also possible to obtain from an image of the spectacle frame 14 taken by the image-pickup camera 62 or the image-pickup camera 63 of the spectacle wearing parameter measurement apparatus 30.

Note that, in the spectacle prescription data Y shown in FIG. 10, "SPH" denotes a spherical diopter (unit: dpt), "CYL" denotes an astigmatic diopter (unit: dpt), "AXS" denotes a cylinder axis (unit: °), "PX" denotes an x-direction prism diopter (unit: Δdpt), "PY" denotes a y-direction prism diopter (unit: Δdpt), and "PD" denotes an inter-pupil distance (unit: mm)

Further, the near vision target distance NL and the eyeball rotation angle θ are already known, those data are inputted into a "near vision distance" field and a "near vision angle" field, respectively, of the data input screen in FIG. 10. In the present embodiment, the eyeball rotation angle θ (in other words, the near vision angle) is designed to be inputted, however, a progressive zone length L (a distance between a distance vision point center and a near vision point center) may be used instead. This is because that the equation below is basically established between the eyeball rotation angle θ and the progressive zone length L, as shown in FIG. 21.

$$L = P \times \tan \theta$$

Here, "P" indicates a distance from the center of the eyeball rotation (center of rotation 12) to the spectacle lens 13, and generally 27 mm is employed. In this case, the above equation is only a basic equation without considering the spectacle frame wearing angle a or the like, and the value of "p" may differ depending on each spectacle wearer, however, the equation can give a certain indication. The eyeball rotation angle θ is calculated using the progressive zone length L to let the spectacle wearer be in the near vision state, and if necessary, a slight adjustment is performed to the eyeball rotation angle θ.

[Positioning in Vertical Direction (S4)]

After the data input, the chin of the test subject 10 is placed on the chin rest 42 of the positioning unit 35 shown in FIG. 3, and the chin rest 42 or the base 37 is moved vertically while the forehead of the test subject 10 is fitted to the forehead support 43; and the eye of the test subject 10 (namely, the spectacle wearer) is adjusted to match with the reference mark 45 of the forehead support column 44 by viewing from the side.

[Image Pickup of Distance Vision State (S5)]

Figure 11:
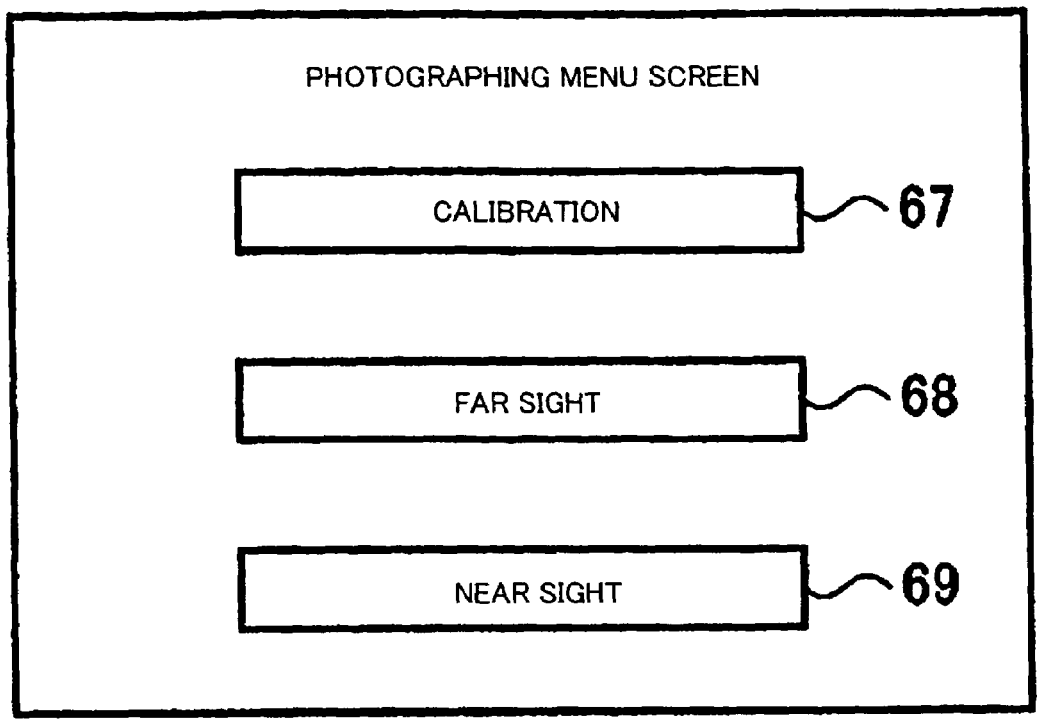
FIG. 11 is a view showing an example image pickup menu screen.

After completing the data input using the data input screen in FIG. 10, the image pickup menu screen shown in FIG. 11 is displayed on the monitor of the device control terminal 32. When a distance vision button 68 of the image pickup menu screen is selected, the light source 56 is lighted on at the distance vision state measurement position in FIG. 6(A). The light source 56 serves as a vision fixing beam. In this distance vision state, when the target distance of the fixing light that the test subject 10 being a spectacle wearer gazes is desired to be set, for example, to be approximately 5 m, then, the light source 56 is moved on the optical axis of the lens 60 and adjusted via the half mirror 61 and the lens 60 so that the image (virtual image) of the light source 56 is formed around 5 m rearward of the half mirror 61 and the lens 60.

Figure 7:
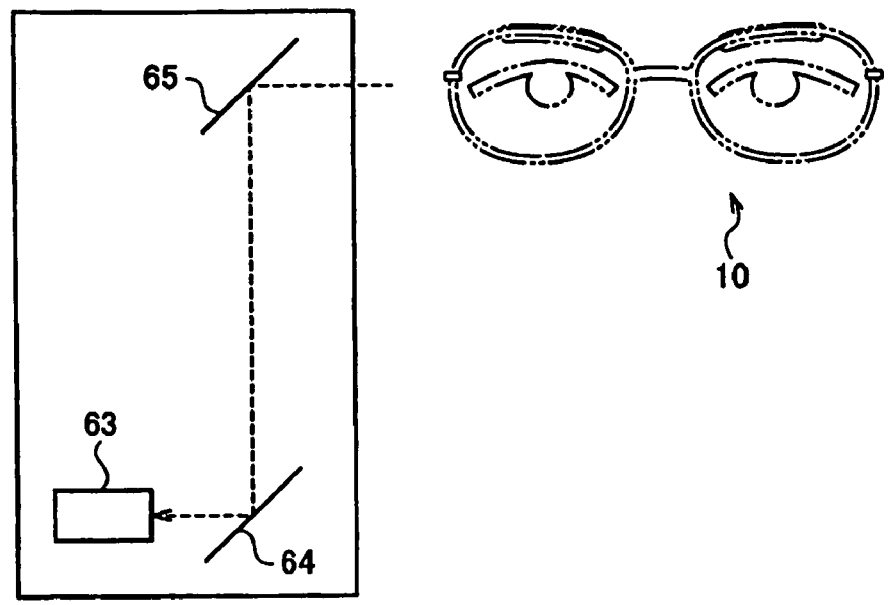
FIG. 7 is a front view schematically showing a state of arranging a side image-pickup camera and mirrors in FIG. 3.
Figure 13:
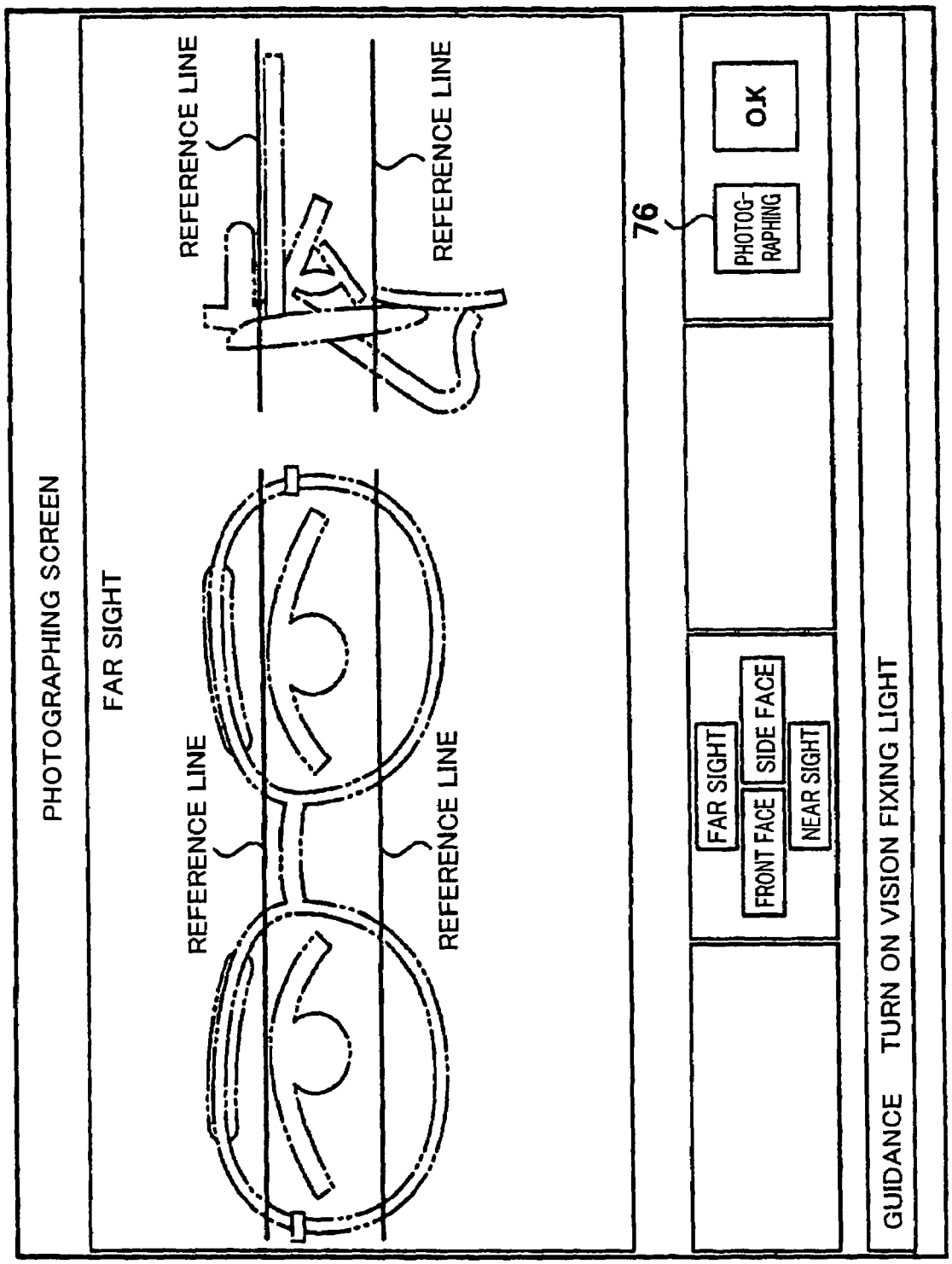
FIG. 13 is a view showing an example image pickup screen for taking an image of the spectacle wearer in a distance vision state.

The test subject 10 observes the optical virtual image as a vision fixing beam, while the examiner confirms that the sight line of the test subject 10 is horizontal and that the face does not tilt through an on-camera screen (distance vision) shown in FIG. 13 and adjusts the height of the base 37 or the seat of the test subject 10 so that the eyes of the test subject 10 comes in an upper and lower reference lines in FIG. 13. After confirming that the test subject's sight line is horizontal and within the upper and lower reference lines, the front face image of the test subject 10 in the distance vision state is taken by the front image-pickup camera 62 by operating an image pickup button 76 displayed on the monitor of the device control terminal 32. At the same time, the side face image of the test subject 10 in the distance vision state is taken by the side image-pickup camera 63 shown in FIG. 3 and FIG. 7.

[Image Pickup of Near Vision State (S6, S7)]

After the front and side face images in the distance vision state are taken, when a near vision button 69 is selected in the image pickup menu screen (FIG. 11) of the device control terminal 32, the movable unit 34 moves in a rotating manner from the distance vision state measurement position in FIG. 6(A) to the near vision state measurement position in FIG. 6(B) along the orbital frames 36 around the center of rotation 12 of the test subject eye 11, and, at the same time, the light source 56 of the movable unit 34 moves on the optical axis of the lens 60 to form an aerial image (real image) and lets the test subject 10 observe the image as a vision fixing beam.

When the eyeball rotation angle θ in the near vision state and the near vision target distance NL of the test subject 10 are already known and those values are already inputted by the data input screen (FIG. 10), there is provided an automatic control, by which the light source 56 being a vision fixing beam is moved in a rotating manner by the movable unit 34 so that the aerial image of the vision fixing beam is formed at the eyeball rotation angle θ and the near vision target distance NL, and at the same time, the light source 56 is moved on the optical axis of the lens 60. After confirming that the test subject 10 observes the vision fixing beam through the on-camera screen (near vision) shown in FIG. 14 and that the eyes of the test subject 10 are within the upper and lower reference lines in FIG. 14, the front face image of the test subject 10 in the near vision state is taken by the front image-pickup camera 62 by operating an image pickup button 77 displayed on the monitor of the device control terminal 32. At the same time, with the side image-pickup camera 63 shown in FIG. 3 and FIG. 7, the side face image of the test subject 10 in the near vision state is taken.

Figure 14:
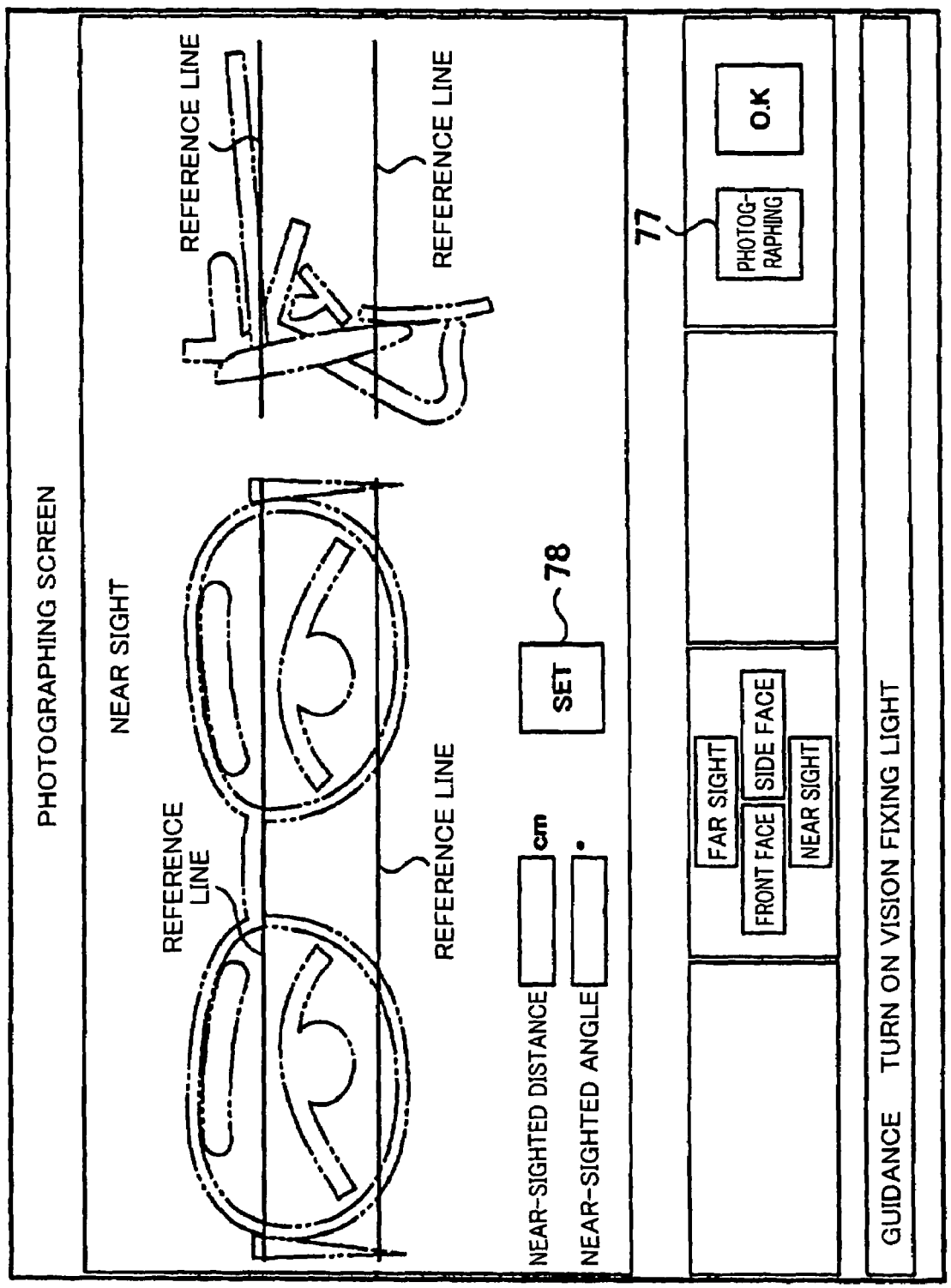
FIG. 14 is a view showing the example image pickup screen for taking the image of the spectacle wearer in a near vision state.

When the eyeball rotation angle θ in the near vision state and the near vision target distance NL of the test subject 10 are unknown, any value is inputted into a "near vision distance" field and a "near vision angle" field of the on-camera screen (near vision) in FIG. 14, respectively, and the light source 56 is moved in a rotating manner as well as on the optical axis of the lens 60 by the movable unit 34 by operating a set button 78 to the extend that the light source 56 comes to a position applicable to the above inputted values. At this state, the eyeball rotation angle θ and the near vision target distance NL are changed so that the test subject 10 can confirm an appropriate near vision state for itself, and the eyeball rotation angle θ and the near vision target distance NL of that near vision state is detected as required eyeball rotation angle θ and near vision target distance NL. After that, the image pickup button 77 is operated to take the frond and side face images of the test subject 10 in the near vision state by the image-pickup cameras 62 and 63, respectively, in the same manner as above.

For instance, as one approach, the eyeball rotation angle θ (near vision angle) is changed by fixing the near vision target distance NL and by moving the light source 56 in a rotating manner by the movable unit 34 to thereby obtain the eyeball rotation angle θ appropriate for the spectacle wearer. After that, the light source 56 is moved on the optical axis of the lens 60 while the eyeball rotation angle θ is kept to change the near vision target distance NL to thereby obtain the appropriate near vision target distance NL, and vice versa.

[Selection of Buttons on Measurement and Comparison Menu Screen (S8)]

Figure 12:
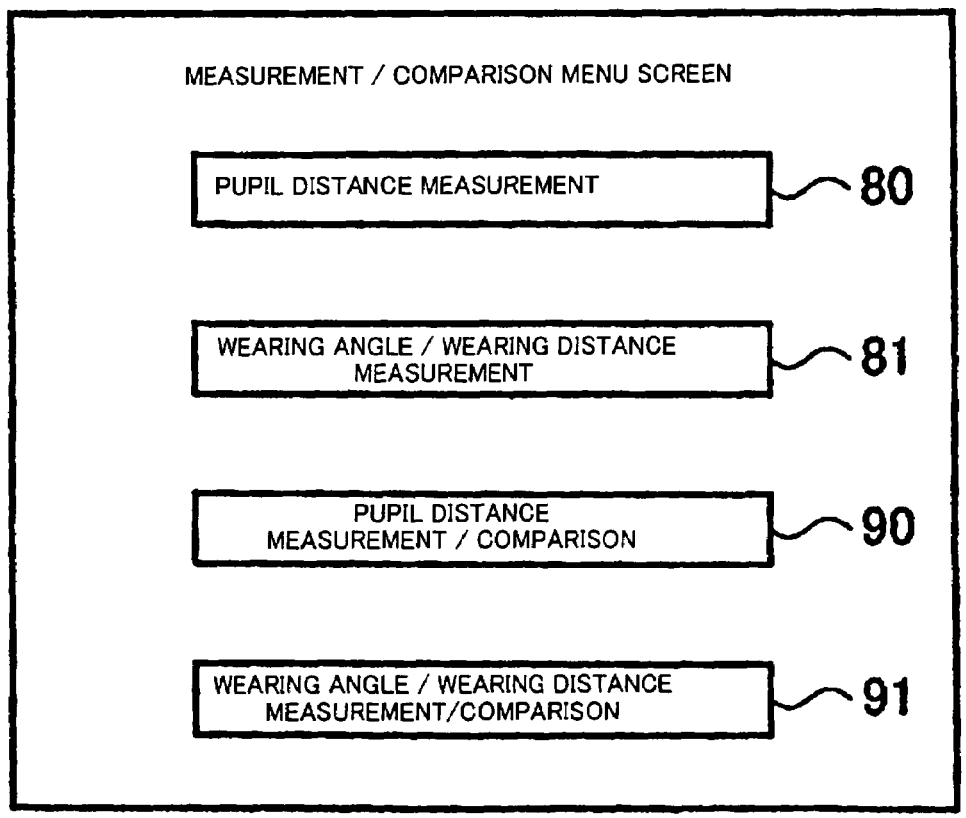
FIG. 12 is a view showing an example measurement and comparison menu screen.

With the images thus acquired, in order to measure and calculate various spectacle wearing parameters required to manufacture the spectacle, each of the measurement programs (FIG. 9) related to the inter-pupil distance measurement button 80 and the spectacle wearing angle and distance measurement button 81 is activated by selecting the relevant button at will in the measurement and comparison menu screen (FIG. 12).

[Measurement and Calculation of Spectacle Wearing Parameter (S9)]

Figure 15:
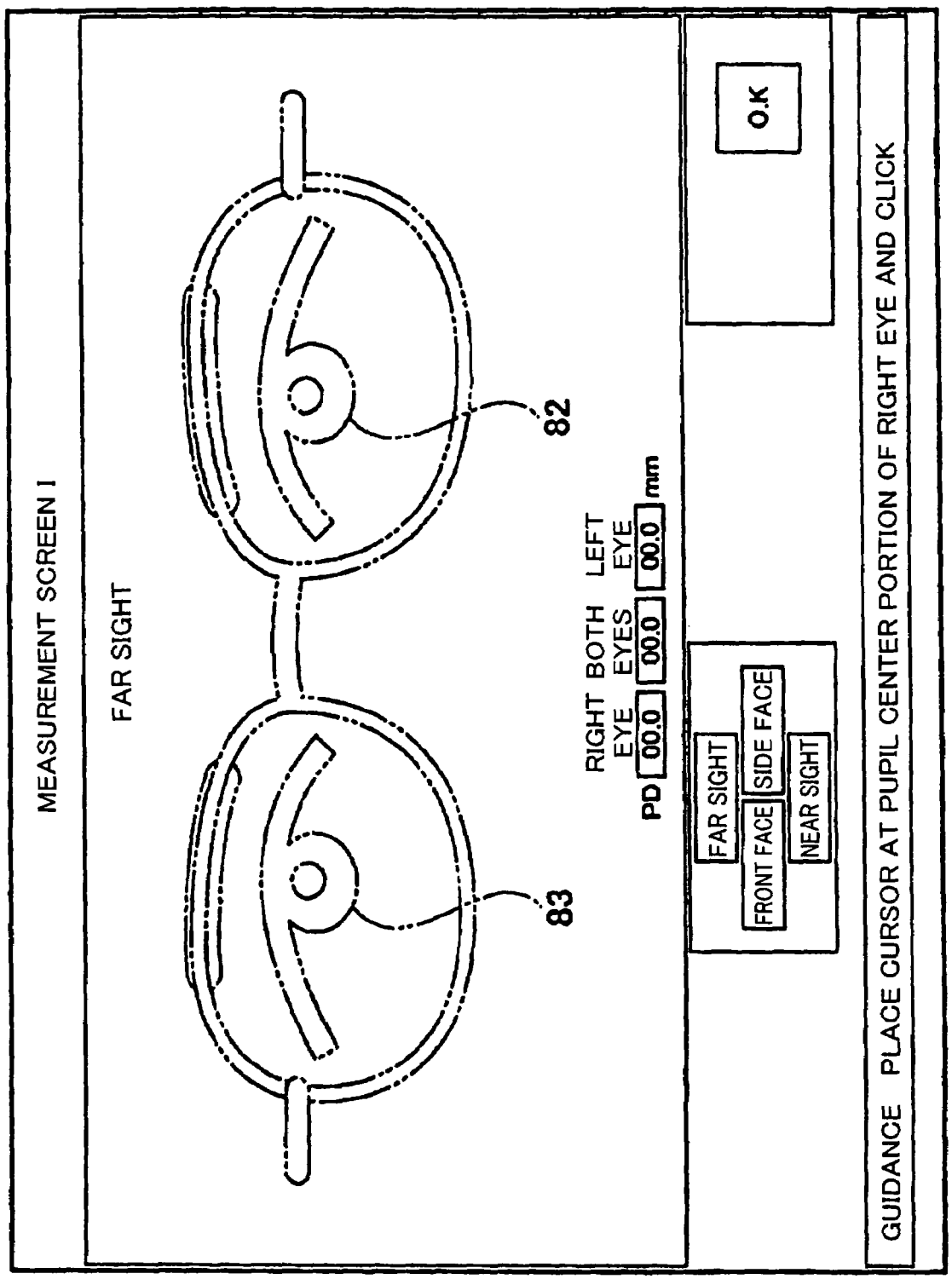
FIG. 15 is a view showing an example measurement screen showing a front face image in the distance vision state of the spectacle wearer.

When the inter-pupil distance measurement button 80 is selected, the inter-pupil distance measurement program is activated, and at the same time, the front image taking the front face of the test subject 10 in the distance vision state is displayed on the monitor of the device control terminal 32, as shown in FIG. 15 and FIG. 16(A). The image is displayed on the monitor after a magnification correction (calibration). Then, the centers of the pupils of the left eye 82 and right eye 83, respectively, are obtained by the measurement method as below as an example, and the distance between both the pupil centers is defined as a distance vision inter-pupil distance FPD.

As a first measurement method, the pupil centers of the left eye 82 and the right eye 83 are directly pointed, respectively, by a pointing device such as a mouse, and the distance on the screen is measured by the device control terminal 32. As a second measurement method, the pupil centers are automatically measured through an image processing. In the second measurement method, in an effort to reduce the processing time, a near-pupil area 89 is drugged by the mouse such as along a dotted line in FIG. 16(A). Next, as to the image, a scanning line 84 of the image is scanned to obtain the change in refracted light amount. The portion of the pupil of the test subject eye (left eye 82, right eye 83) is dark, so that the reflected light amount largely lowers at the pupil portion as shown in FIG. 16(B). Therefore, the lowered portions of the reflected light amount are detected as pupil areas and accordingly the pupil centers are obtained, and then the inter-pupil distance is converted to obtain the distance vision inter-pupil distance FPD.

In the present embodiment, the pupil center can be obtained by any method, namely the first measurement method, the second measurement method, or the other method. Further, the distance vision inter-pupil distance can be obtained by pointing the center of the face (for example, the center of a column of nose) or the center of the bridge 19 of the spectacle frame by the pointing device or the like, and by defining the respective distances from the pointed center to the pupil centers of the left eye 82 and the right eye 83, as a left FPD, right FPD, respectively.

Figure 17:
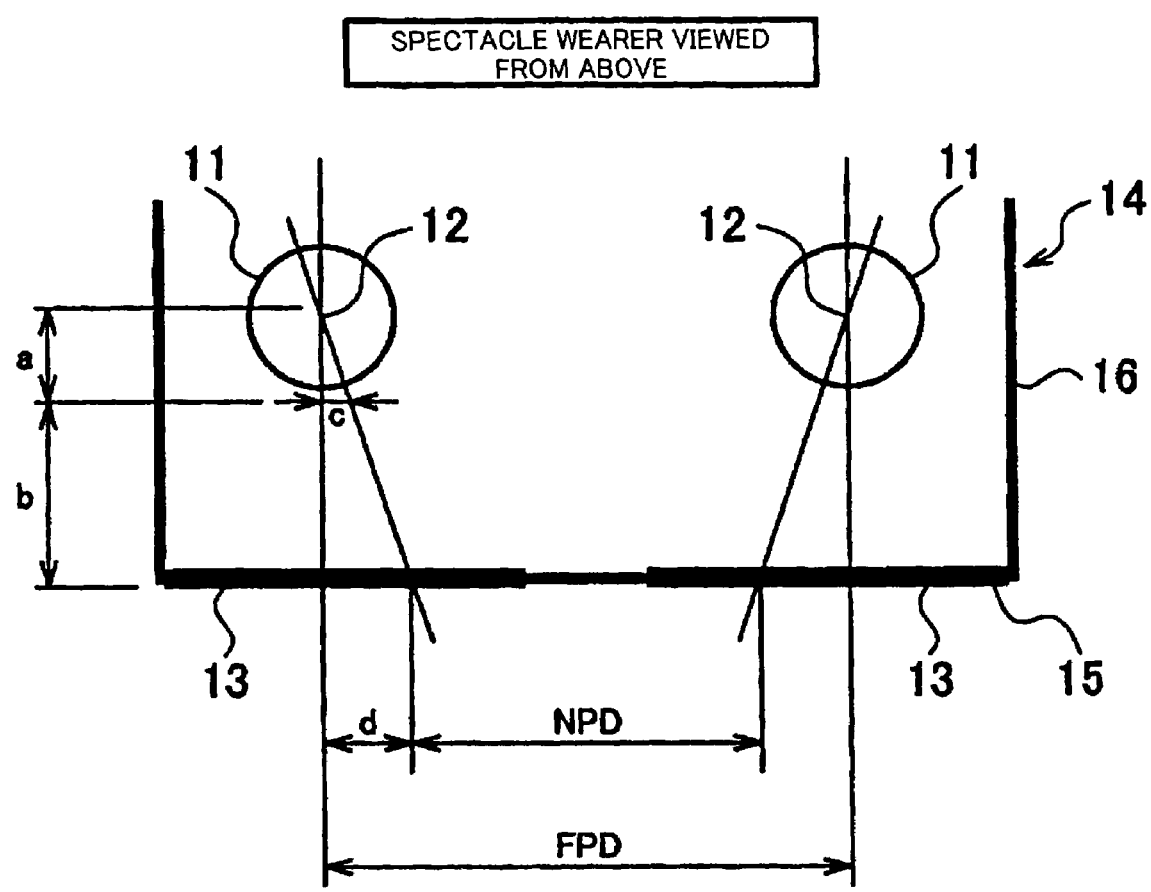
FIG. 17 is an explanation view showing a calculation method for obtaining a near vision inter-pupil distance.

Although the near vision inter-pupil distance NPD can be obtained in the similar operation, differently from the distance vision state, in the near vision state, the sight lines are turned inwards due to convergence. Therefore, the near vision inter-pupil distance NPD obtained in the same manner as of the distance vision inter-pupil distance is only a distance on the test subject eyes 11. Referring to FIG. 17, when manufacturing the spectacle lens 13, it is required to calculate such a point on the surface of the spectacle lens 13 fitted into a rim 15 of the spectacle frame 14 that the sight line passes through in the near vision state, and the near vision inter-pupil distance on the surface of the spectacle lens 13 is the near vision inter-pupil distance NPD to be obtained.

The method to obtain the near vision inter-pupil distance NPD on the surface of the spectacle lens 13 with the obtained front face image will be described with reference to FIG. 17. For simplifying the description, the frame horizontal tilt angle β and the spectacle frame wearing angle a (described later) are defined to be 0 (zero) °, respectively, here. In FIG. 17, if the distance from a corneal vertex to the center of rotation 12 in the test subject eye 11 is defined as "a" (corresponding to "VR" in FIG. 21), the distance vision spectacle wearing distance is defined as "b" (corresponding to "A" in FIG. 21), and a difference between a corneal vertex position in the distance vision state and the corneal vertex position in the near vision state in view of the distance is defined as "c", then an inward eccentric quantity "d" can be expressed by the equation below.

$$d = c(a+b)/a$$

When the distance vision inter-pupil distance and the near vision inter-pupil distance on the surface of the spectacle lens 13 are defined as "FPD" and "NPD", respectively, the distance vision inter-pupil distance FPD equals to the inter-pupil distance of the front image in the distance vision state, so that the near vision inter-pupil distance NPD can be expressed by the equation below.

$$NPD = FPD - 2 \cdot d$$

Here, for the distance "a" from the corneal vertex to the center of rotation 12, generally 13 mm is employed frequently, however, any other value is acceptable. In order to obtain a more accurate near vision inter-pupil distance NPD, the correction is required using the frame horizontal tilt angle β and the spectacle frame wearing angle a, whereas the correction is omitted here.

Next, the spectacle wearing angle and distance measurement button 81 is selected in the measurement and comparison menu (FIG. 12) of the device control terminal 32. Then, the spectacle frame wearing angle measurement program (FIG. 9) is activated first, and at the same time, as shown in FIG. 18(A), the side face image of the test subject 10 in the distance vision state and after the magnification correction is displayed on the monitor of the device control terminal 32. The side face image is used to measure the spectacle frame wearing angle a and the distance vision spectacle wearing distance A. The corneal vertexes of the test subject eyes 11 are pointed by the pointing device such as the mouse, on the screen shown in FIG. 18(A), and a horizontal line is drawn to draw the optical axis, namely the distance vision axis 17. The spectacle frame wearing angle a is the angle formed by the rim 15 of the spectacle frame 14 and a vertical straight line 85 being orthogonal to the optical axis (distance vision axis 17). In order to determine the spectacle frame wearing angle a, two or four points are pointed along the side surface shape of the rim 15 of the spectacle frame 14 by the pointing device such as a mouse; a straight line 86 is displayed by calculation based on these coordinate values; and the angle formed by the straight line 86 and the previously-described straight line 85 is defined as the spectacle frame wearing angle a.

After the measurement of the spectacle wearing frame angle a, the spectacle wearing distance measurement program (FIG. 9) is activated. Since the spectacle frame wearing angle a is already known, first, a reference straight line 87 in parallel with the spectacle frame wearing angle a and passing through the corneal vertex is displayed. A straight line 88 in parallel with the reference straight line 87 is generated on the screen, and the straight line 88 is moved parallel by the pointing device such as the mouse up to the position of the rim 15 of the spectacle frame 14. Then, the distance between the straight line 88 having moved to the position of the rim 15 and the reference straight line 87 is measured and the measured distance is defined as a tentative wearing distance. The actual distance vision spectacle wearing distance A is affected by a three dimensional shape of the spectacle such as the frame horizontal tilt angle β, a lens curve, and the like, so that the spectacle wearing distance measurement program reads a trace data or the lens curve of the spectacle frame 14 and makes calculation to obtain the distance vision spectacle wearing distance A by considering the calculation value and the above-described tentative wearing distance.

The near vision spectacle wearing distance B can also be obtained in the similar operation. Specifically, since the eyeball rotation angle θ is already known, the corneal vertex of the test subject eye 11 is pointed by the pointing device such as a mouse, and an optical axis in accordance with the eyeball rotation angle θ, namely the near vision axis 18 is drawn. The distance between the corneal vertex on the optical axis and the rim 15 of the spectacle frame 14 is measured to be defined as the tentative wearing angle. The actual near vision spectacle wearing distance B is affected by the three dimensional shape of the spectacle such as the frame horizontal tilt angle β, the lens curve, and the like, so that the trace data or the lens curve of the spectacle frame 14 are read to calculate and obtain the near vision spectacle wearing distance B by considering the calculation value and the above-described tentative wearing distance.

Next, a method to reduce an image pickup failure by way of detecting blinking will be described. It is said that blinking is performed irregularly for about 0.1 second each. It is possible to persuade the spectacle to refrain from blinking, yet, blinking is performed unconsciously by nature, so that the prevention is not easy.

Accordingly, first, it is confirmed by an examiner that the sight line (distance vision axis 17) of the test subject 10 is in the horizontal direction through the monitor or the like by letting the test subject 10 being a spectacle wearer observe the image of the light source 56 (see FIG. 13). When the sight line is not horizontal, the height of the base 37 or the seat on which the test subject 10 is seated is adjusted to make the sight line be horizontal. Next, it is confirmed that the eyes of the test subject 10 are within the upper and lower reference lines in the on-camera screen (FIG. 13) on the monitor of the device control terminal 32, and when the eyes are within the reference lines, the image pickup button 76 is pushed. Then, the device control terminal 32 performs an image processing as in FIG. 16(B) in real time so as to determine the positions of the pupils in the area within both the reference lines to thereby find the pupils, and at the same time, detects the change in the reflected light amount in the pupils. Since the reflected light amount is larger in an eyelid than in the corneal, blinking leads a large increase in the reflected light amount, so that blinking can be detected. When the image pickup button 76 in the on-camera screen (FIG. 13) displayed on the monitor for taking the face images of the test subject 10 is operated, and when the device control terminal 32 detects blinking, then the device control terminal 32 displays a "rephotograph" indicator in the screen, while the face images are taken by the front image-pickup camera 62 and the side image-pickup camera 63 to be recorded when no blinking is detected.

Note that the device control terminal 32 may display the indicator "rephotograph" in the screen, while the device control terminal 32 may be designed to take the images by automatically detecting a moment when no blinking is performed instead of displaying such an indicator. The image pickup failure is thus reduced by detecting blinking by the device control terminal 32, so that the spectacle wearing parameter measurement apparatus 30 can reduce the measurement time. The device control terminal 32 detects blinking in the above-described manner also when taking the face images of the test subject 10 in the near vision state.

[Data Storage (S10)]

The device control terminal 32 stores the spectacle wearing parameter V acquired in the above-described manner, together with the customer personal data X and the spectacle frame data Z, for example, in the device control terminal 32 and in the customer database 71 in the form of a listing in a save screen shown in FIG. 19, and then the taken images are stored as well. In the save screen, the progressive zone length L (distance between the distance vision point center and the near vision point center) in the spectacle lens targeting seniors such as a progressive-power lens is determined using the above-described distance vision and near vision spectacle wearing parameters to be displayed.

Specifically, since the distance vision spectacle wearing distance A, the near vision spectacle wearing distance B, the spectacle frame wearing angle a, and the eyeball rotation angle θ as shown in FIG. 21 are already measured and calculated, the device control terminal 32 calculates the progressive zone length L on the assumption that the distance VR from the corneal vertex to the center of rotation 12 of the eyeball is 13 mm. The progressive zone length L is a necessary and important parameter in designing the progressive-power lens optimal to the spectacle wearer in addition to it is useful in selecting the type of the progressive-power lenses. Note that the distance from the corneal vertex to the center of rotation 12 of the test subject eye 11 is defined to be 13 mm here, however, this is a figure commonly used for a Japanese, and for the case of a European, 14 mm is employed largely. Further, in FIG. 21, a shown case is that the progressive surface is on an eye side of the spectacle lens 13, however, when the progressive surface is on an object side of the spectacle lens 13, the progressive zone length L is calculated in consideration of the lens thickness.

[Order Placement of Spectacle Lens and Spectacle (S11)]

The individual spectacle wearers data required to manufacture the spectacle (at least, one of the customer personal data X, the spectacle lens data W, the spectacle prescription data Y, the spectacle frame data Z, the spectacle wearing parameter V, and the processing instruction data) stored in the customer database 71 and the device control terminal 32 of the spectacle wearing parameter measurement apparatus 30 (FIG. 1) is transmitted from the spectacle store terminal 70 to the factory server 101 of the spectacle manufacturer to thereby be stored in the customer database 103, so that the order for the spectacle lens or the spectacle is placed. Because of this, based on the respective spectacle wearers data required to manufacture the spectacle (at least, one of the customer personal data X, the spectacle lens data W, the spectacle prescription data Y, the spectacle frame data Z, the spectacle wearing parameter V, and the processing instruction data) used in the spectacle glasses shop 100, the factory server 101 performs an optical designing of a spectacle lens optimal to each of the spectacle wearers, manufactures the spectacle lens based on the design values, sets the spectacle lens, and thereby manufactures the optimal spectacle for the spectacle wearer.

The spectacle lens targeting a presbyopia such as a progressive-power lens requires the distance vision and near vision spectacle wearing parameters, however, in the case of a single vision lens dedicated to the near vision, the distance vision spectacle wearing parameter is not necessary, so that the image pickup in the distance vision state can be omitted. Also, in the case of the single vision lens for the distance vision or the near vision, the spectacle wearing parameter for the near vision is not necessary, so that the image pickup in the near vision state can be omitted. Thus, depending on the type the spectacle lens worn by the spectacle wearer, the spectacle wearing parameter is selected and measured by the spectacle wearing parameter measurement apparatus 30 arbitrarily to thereby be transmitted from the spectacle store terminal 70 to the factory server of the spectacle manufacturer.

[Starting Measurement and Comparative Verification Activities (S12) to Comparative Verification (S14)]

In order to confirm whether or not the worn state of the manufactured spectacle is appropriate for the spectacle wearer, a comparison is made between the distance vision inter-pupil distances FPD, the near vision inter-pupil distances NPD, the distance vision spectacle wearing distances A, the near vision spectacle wearing distances B and the spectacle frame wearing angles a before and after the fabrication of the spectacle. For the comparison, first, the manufactured spectacle is put on the spectacle wearer, the face images in the distance vision state and near vision state are taken by the front image-pickup camera 62 and the side image-pickup camera 63 (S5, S7), and the taken images are stored in the device control terminal 32. When taking the image in the near vision state, the vision fixing beam is set at the same eyeball rotation angle θ and the near vision target distance NL as those applied to take the images before manufacturing the spectacle.

After the above-descried face images are taken, in the measurement and comparison menu screen (FIG. 12) displayed on the monitor of the device control terminal 32, any of an inter-pupil distance measurement and comparison button 90 and a wearing angle and wearing distance measurement and comparison button 91 is selected to activate respective measurement and comparative verification program software.

When the inter-pupil distance measurement and comparison button 90 is selected, an inter-pupil distance measurement and comparative verification program software is activated, and at the same time, as shown in FIG. 16(C), the front face image of the spectacle wearer wearing the manufactured spectacle and in the distance vision state is displayed on the monitor of the device control terminal 32. The image is displayed on the monitor after a magnification correcting (calibration).

The right and left optical centers of the spectacle lens is marked beforehand using a lens mater. In the case of a decentered lens, the making is performed by considering the decentered state. In the front face image, the marked optical centers of the spectacle lens are clicked by the pointing device such as a mouse to obtain the coordinates of the optical centers, and the inter-pupil distance is obtained with the coordinate values to be defined as the distance vision inter-pupil distance FPD. Further, since pupil portions of the left eye 82 and the right eye 83 are dark, it is also possible that a reflected light amount change is obtained by scanning the scanning line 84 in the front face image, a largely dropping portion in the reflected light amount is defined as the pupil area as shown in FIG. 16(B), the pupil center is thereby obtained, the distance between the pupil centers is converted into a distance, and thus the distance vision inter-pupil distance FPD is obtained.

The activated inter-pupil distance measurement and comparative verification program software displays the distance vision inter-pupil distance FPD measured after manufacturing the spectacle as described above in a "FPD after spectacle fabrication" field in FIG. 16(C) in figures, and in a "FPD before spectacle fabrication" field, the distance vision inter-pupil distance FPD of the same spectacle wearer measured for manufacturing the spectacle before manufacturing the spectacle and stored in the customer database 71 or the customer database 103 is displayed in figures. The inter-pupil distance measurement and comparative verification program software in operation compares both the distance vision inter-pupil distances FPD by displaying the two in a line to verify by determining whether or not the figure of the distance vision inter-pupil distance FPD after the spectacle fabrication is within an allowable range as compared to the figure of the distance vision inter-pupil distance FPD before the spectacle fabrication.

Note that a left FPD and a right FPD indicating the distances from the center of the face or the center of the spectacle frame bridge to the optical center of the left/right spectacle lens or the left/right pupil center, respectively, may be comparatively verified before and after the spectacle fabrication, instead.

The activated inter-pupil distance measurement and comparative verification program software measures the near vision inter-pupil distance NPD after the spectacle fabrication in the same manner as the measurement and calculation and determination procedures for the near vision inter-pupil distance NPD before the spectacle fabrication, and these before and after near vision inter-pupil distances NPD are displayed in the monitor in figures for comparison, even though they are not shown here, to verify by determining whether or not the figure of the near vision inter-pupil distance NPD after the spectacle fabrication is within an allowable range as compared to the figure of the near vision inter-pupil distance NPD before the spectacle fabrication.

In the measurement and comparison menu in FIG. 12, when the wearing angle and wearing distance measurement and comparison button 91 is selected, first, a spectacle frame wearing angle measurement and comparative verification program software (FIG. 9) is activated; and at the same time, as shown in FIG. 18(B), the side image in the distance vision state after a magnification correction is displayed on the monitor of the device control terminal 32. The activated spectacle frame wearing angle measurement and comparative verification program software measures the spectacle frame wearing angle a after manufacturing the spectacle in the above-described side image on the monitor in the same procedures as measuring the spectacle frame wearing angle a before manufacturing the spectacle, and the spectacle frame wearing angle a is displayed in figures at a relevant field applicable to a "wearing angle" column and an "after spectacle fabrication" line in FIG. 18(B). Further, the spectacle frame wearing angle measurement and comparative verification program software in operation displays the spectacle frame wearing angle a of the same spectacle wearer before manufacturing the spectacle and imported from the customer database 71 or the customer database 103 in the relevant field applicable to the "wearing angle" column and a "before spectacle fabrication" line in FIG. 18(B) in figure, compares these spectacle frame wearing angles a using figures, and verifies by determining whether or not the spectacle frame wearing angle a after the spectacle fabrication is within an allowable range as compared to the spectacle frame wearing angle a before the spectacle fabrication.

After the measurement and comparative verification of the spectacle frame wearing angle a after manufacturing the spectacle, a spectacle wearing distance measurement and comparative verification program software is activated. The program software, at the side image of the FIG. 18(B), measures the distance vision spectacle wearing distance A after the spectacle fabrication in the same procedures as measuring the distance vision spectacle wearing distance A before the spectacle fabrication, and displays the distance vision spectacle wearing distance A in the field applicable to a "wearing distance" column and the "after spectacle fabrication" line in FIG. 18(B) in figure. Further, the spectacle wearing distance measurement and comparative verification program software in operation displays the distance vision spectacle wearing distance A of the same spectacle wearer before the spectacle fabrication and imported from the customer database 71 or the customer database 103, in the field applicable to the "wearing distance" column and the "before spectacle fabrication" line in figure, and verifies by determining whether or not the distance vision spectacle wearing distance A after the spectacle fabrication is within an allowable range as compared to the distance vision spectacle wearing distance A before the spectacle fabrication.

The spectacle wearing distance measurement and comparative verification program software in operation measures the near vision spectacle wearing distance B after the spectacle fabrication in the same measurement, calculation, and determination procedures as measuring the near vision spectacle wearing distance B before the spectacle fabrication, and, even though it is not shown here, these near vision spectacle wearing distances B before and after the spectacle fabrication are displayed on the monitor in figures and compared, and verified by determining whether or not the figure of the near vision spectacle wearing distance B after the spectacle fabrication is within an allowable range as compared to the near vision spectacle wearing distance B before the spectacle fabrication.

[Data Storing (S15) and So Forth]

When the respective distance vision inter-pupil distance FPD, near vision inter-pupil distance NPD, distance vision spectacle wearing distance A, near vision spectacle wearing distance B, and spectacle frame wearing angle a, after the spectacle manufacture are determined and verified to be within the allowable range as compared to the respective distance vision inter-pupil distance FPD, near vision inter-pupil distance NPD, distance vision spectacle wearing distance A, near vision spectacle wearing distance B, and spectacle frame wearing angle a before the spectacle manufacture; the device control terminal 32 determines that the wearing state of the manufactured spectacle is appropriate for the spectacle wearer and the spectacle is acceptable, and stores the respective distance vision inter-pupil distances FPD, near vision inter-pupil distances NPD, distance vision spectacle wearing distances A, near vision spectacle wearing distances B, and spectacle frame wearing angles a before and after the spectacle fabrication and a comparative data of these spectacle wearing distance parameters before and after the spectacle fabrication together with the taken images in the customer database 71 and/or the customer database 103.

When the respective distance vision inter-pupil distance FPD, near vision inter-pupil distance NPD, distance vision spectacle wearing distance A, near vision spectacle wearing distance B, and spectacle frame wearing angle a after the spectacle fabrication are determined and verified to be not within the allowable range as compared to the respective distance vision inter-pupil distance FPD, near vision inter-pupil distance NPD, distance vision spectacle wearing distance A, near vision spectacle wearing distance B, and spectacle frame wearing angle a before the spectacle fabrication, the device control terminal 32 displays an indication prompting a spectacle fitting work adjusting the spectacle frame. The examiner executes the spectacle fitting work and repeats Steps S4 to S8 and Steps S12 to S14 using the spectacle wearing parameter measurement apparatus 30 to the extent that the spectacle is determined to be acceptable. At this time, since the comparative data before and after the spectacle fabrication is stored in the customer database 71 or the customer database 103, the fitting work can be executed easily by using the comparative data.

Since it is configured as described above, according to the above embodiment, the advantages (1) to (13) described below are effected.

(1) The spectacle store terminal 70 in a spectacle lens supply system 102 is configured to be capable of exchanging information, namely the personal data of the spectacle wearer (at least, one of the customer personal data X, the spectacle lens data W, the spectacle prescription data Y, the spectacle frame data Z, the spectacle wearing parameter V, and the processing instruction data) including the spectacle wearing parameter and required to manufacture the spectacle, with the factory server 101; so that the factory server 101 can supply an optimal and dedicated spectacle lens or the spectacle for each spectacle wearer by receiving the personal data of the spectacle wearer, which includes the spectacle wearing parameter and is required to manufacture the spectacle, from the spectacle store terminal 70 and by utilizing them in manufacturing the spectacle lens or the spectacle.

(2) The personal data of the respective spectacle wearers (at least, one of the customer personal data X, the spectacle lens data W, the spectacle prescription data Y, the spectacle frame data Z, the spectacle wearing parameter V, and the processing instruction data) required to manufacture the spectacle and including the spectacle wearing parameter is recorded and stored in the customer database 71 and the customer database 103 of the spectacle store terminal 70 and the factory server 101, respectively, in a spectacle lens providing system 100, so that the customer database 71 and the customer database 103 works effectively when the spectacle wearer orders a new spectacle, when the spectacle wearer orders a spectacle with a changed prescription, or when the ordering side such as a spectacle store, an eye clinic, an individual, or the like updates the record related to the spectacle of the customer being a spectacle wearer.

(3) The personal data of the respective spectacle wearers (at least, one of the customer personal data X, the spectacle lens data W, the spectacle prescription data Y, the spectacle frame data Z, the spectacle wearing parameter V, and the processing instruction data) required to manufacture the spectacle and including the spectacle wearing parameter is recorded and stored in the customer database 71 and the customer database 103 in the spectacle lens providing system 100, so that the spectacle lens or the spectacle being optimal for and dedicated to each of the respective spectacle wearers can be supplied when the factory server 101 uses the data stored in the customer database 71 and the customer database 103 for the manufacture of the spectacle lens or the spectacle.

(4) In the spectacle wearing parameter measurement apparatus 30, the movable unit 34 having the light source 56 and the lens 60 sets the test subject 10 being a spectacle wearer to be in the distance vision state or the near vision state and, in the near vision state, at least one of the eyeball rotation angle $\theta$ and the near vision target distance NL is designed to be arbitrarily changeable, where the images of the test subject 10 set in the distance vision state or in the near vision state are taken by the front image-pickup camera 62 and the side image-pickup camera 63, and then the spectacle wearing parameter is measured and calculated based on the obtained images by the device control terminal 32, so that the spectacle wearing parameters in the distance vision and near vision can be measured with high accuracy. As a result, the spectacle lens optimal for and dedicated to each spectacle wearer can be optically designed using, at least, one of the spectacle parameters measured with high accuracy by the spectacle wearing parameter measurement apparatus 30, and the spectacle optimal for and dedicated to each spectacle wearer can be manufactured by setting the spectacle lens therein.

(3) The spectacle wearing parameter measurement apparatus 30 can measure the spectacle wearing parameter in both the distance vision state and near vision state, allowing the required spectacle wearing parameter to be selected depending on the spectacle lens type worn by the spectacle wearer, so that the measurement time by the spectacle wearing parameter measurement apparatus 30 can be reduced by omitting the measurement of unnecessary spectacle wearing parameter.

(6) The spectacle wearing parameter measurement apparatus 30 sets the distance vision state and near vision state of the test subject 10, by maintaining the optical axis of the front image-pickup camera 62 to always match with the distance vision axis 17 or the near vision axis 18 of the test subject eye 11 of the test subject 10 being a spectacle wearer positioned by the movable unit 34, and by moving the front image-pickup camera 62 in a rotating manner around the center of rotation 12 of the test subject eye 11 of the test subject 10, so that the front image-pickup camera 62 can take the image of the test subject 10 appropriately even in the near vision state in the same manner as in the distance vision state, allowing a highly accurate measurement of the spectacle wearing parameter on the basis of this taken image.

(7) In the spectacle wearing parameter measurement apparatus 30, when the eye rotation angle $\theta$ and the near vision target distance NL are unknown, the eye rotation angle $\theta$ and the near vision target distance NL are determined by moving the movable unit 34 having the light source 56 and the lens 60 in a rotating manner along the orbital frames 36 and, at the same time, moving the light source 56 to approach and leave to/from the lens 60,. while letting the test subject 10 being a spectacle wearer confirm an appropriate near vision state, so that the eye rotation angle θ and the near vision target distance NL optimal for the spectacle wearer can be measured with high accuracy.

(8) In the spectacle wearing parameter measurement apparatus 30, the distance vision spectacle wearing distance A and the near vision spectacle wearing distance B are calculated in consideration of the three dimensional shape such as the frame horizontal tilt angle β of the spectacle frame 14 or the like, so that these distance vision spectacle wearing distance A and near vision spectacle wearing distance B can be measured with high accuracy by modifying the respective measured wearing distances based on the three dimensional shape.

(9) In the spectacle wearing parameter measurement apparatus 30, the near vision inter-pupil distance NPD is calculated based on the surface of the spectacle lens 13 of the spectacle worn by the test subject 10 being a spectacle wearer, so that an optimal value can be measured and obtained for the near vision inter-pupil distance NPD required to manufacture the spectacle.

(10) In the spectacle wearing parameter measurement apparatus 30, the vision fixing beam in the distance vision state set by the light source 56 in the movable unit 34 is formed as a virtual image, so that the spectacle wearing parameter measurement apparatus 30 can be downsized as compared to the case where a real image is formed as a vision fixing image in the distance vision state.

(11) The device control terminal 32 in the spectacle wearing parameter measurement apparatus 30 detects blinking of the test subject 10 being a spectacle wearer to thereby take the image of the test subject 10 when the test subject 10 does not blink, so that the failure in the face image pickup of the test subject 10 can be reduced, allowing the spectacle wearing parameter measurement apparatus 30 to reduce the measurement time of the spectacle wearing parameter.

(12) The spectacle lens is manufactured through an optical designing using the personal data of the respective spectacle wearers (at least, one of the customer personal data X, the spectacle lens data W, the spectacle prescription data Y, the spectacle frame data Z, the spectacle wearing parameter V, and the processing instruction data) required to manufacture the spectacle and including the spectacle wearing parameter measured by the spectacle wearing parameter measurement apparatus with high accuracy, so that the spectacle lens can be the spectacle lens optimal for and dedicated to each spectacle wearer, and the spectacle can be the spectacle optimal for and dedicated to each spectacle wearer, as well.

(13) The device control terminal 32 of the spectacle wearing parameter measurement apparatus 30 measuring the spectacle wearing parameter required to manufacture the spectacle appropriate for the spectacle wearer serves as a comparison means comparing the spectacle parameters measured at present time after manufacturing the spectacle (the distance vision inter-pupil distance FPD, the near vision inter-pupil distance NPD, the distance vision spectacle wearing distance A, the near vision spectacle wearing distance B, and the spectacle frame wearing angle a, respectively) with the spectacle parameters of the same spectacle wearer measured before manufacturing the spectacle and stored in the customer database 71 and the customer database 103 (the distance vision inter-pupil distance FPD, the near vision inter-pupil distance NPD, the distance vision spectacle wearing distance A, the near vision spectacle wearing distance B, and the spectacle frame wearing angle a, respectively) with figures, and further serves as a verification means verifying by determining the spectacle wearing state to be appropriate or inappropriate based on the figures obtained by the comparison means, so that the spectacle wearing state of the newly manufactured spectacle can be compared appropriately and objectively based on figures, allowing a speedy and accurate verification of the wearing state of the spectacle.

As has been described in above, the present invention has been described based on the above embodiment, whereas the present invention is not limited thereto.

For instance, in the above embodiment, the description has been given of the embodiment in which the wearing state of the manufactured spectacle is compared and verified to be appropriate or inappropriate using the spectacle wearing parameter measurement apparatus 30 after manufacturing the spectacle, whereas the spectacle wearing parameter measurement apparatus 30 may be used to check the wearing state of the spectacle when performing a maintenance of the spectacle after the spectacle is bought by a customer.

In other words, the appropriateness of the spectacle wearing state at the time of the maintenance may be determined and verified by measuring the spectacle wearing parameter (the distance vision inter-pupil distance FPD, the near vision inter-pupil distance NPD, the distance vision spectacle wearing distance A, the near vision spectacle wearing distance B, and the spectacle frame wearing angle a, respectively) at the time of the maintenance, and by comparing the spectacle wearing parameter at the time of the maintenance with the spectacle wearing parameter of the same spectacle wearer measured therebefore (before or right after the spectacle manufacture, or the like) and stored in the customer database 71 or the customer database 103.

Specifically, after a customer bought a spectacle, and when the customer has a different feeling in wearing the spectacle or when the spectacle is deformed for any reason, it is possible to verify the wearing state of the spectacle using the spectacle wearing parameter measurement apparatus 30 and the customer database 71 or the customer database 103, allowing a determination whether or not the wearing state of the spectacle is not good, or whether or not the prescription of the spectacle lens fits the spectacle wearer. When the wearing state of the spectacle is not good, a fitting work is performed for the spectacle so that the spectacle wearing parameter at the time of the maintenance comes into an allowable range as compared to the spectacle wearing parameter measured before the maintenance, for example, before the spectacle manufacture; and when the prescription of the lens comes not to fit the spectacle wearer, an eye sight test is conducted to review the prescription values. Further, as one customer service in the spectacle store or the like, it can be used for a periodical check for wearing the spectacle.

Further, in the above embodiment, the spectacle store terminal 70 and the factory server 101 referred to are those connected to each other via a communication line such as an Internet, however, they may be connected via a dedicated line. Furthermore, the network connecting the spectacle store terminal 70 and the factory server 101 may be the one having a network server therebetween, or the one having the network server and plural other factories' severs 101 therebetween. Moreover, the spectacle store terminal 70 and the factory server 101 may be connected by a telephone line.

Further, in the above embodiment, the spectacle store terminal 70 referred to is the spectacle store terminal 70 connected to the device control terminal 32 of the spectacle wearing parameter measurement apparatus 30, whereas the spectacle store terminal 70 may not be connected to the device control terminal 32 and the spectacle wearing parameter V may be measured by the spectacle wearing parameter measurement apparatus 30 and inputted by hand or the other input means to be recorded and stored in the customer database 71.

Still further, in the above embodiment, a light source such as a LED is used and the image of the light source is used as a vision fixing beam, whereas any image such as a character, mark, or the like may be used instead.

The invention claimed is:

1. A spectacle wearing parameter measurement apparatus measuring a spectacle wearing parameter required to manufacture a spectacle suited to a spectacle wearer, comprising:
   a vision fixing means setting the spectacle wearer wearing a spectacle frame to be in a distance vision state or a near vision state and, in the near vision state, at least one of an eyeball rotation angle and a near vision target distance can be changed optionally,
   an image input means taking an image of the spectacle wearer set in the distance vision state or the near vision state by said vision fixing means using an image pickup device to import the image; and
   a measurement and calculation means measuring and calculating the spectacle wearing parameter based on the taken image obtained by said image input means.

2. The spectacle wearing parameter measurement apparatus according to claim 1,
   wherein the spectacle wearing parameter measured and calculated by said measurement and calculation means is, at least one of a distance vision inter-pupil distance, a near vision inter-pupil distance, a distance vision spectacle wearing distance, a near vision spectacle wearing distance, a spectacle frame wearing angle, an eyeball rotation angle and a near vision target distance.

3. The spectacle wearing parameter measurement apparatus according to claim 1,
   wherein said vision fixing means moves in a rotating manner around a center of rotation of an eyeball by being interlocked with the image pickup device to always keep an optical axis of the image pickup device match with an axis of sighting of the eyeball.

4. The spectacle wearing parameter measurement apparatus according to claim 1,
   wherein, of the spectacle wearing parameter, the eyeball rotation angle and the near vision target distance are measured by being changed and determined by said vision fixing means while letting the spectacle wearer confirm an appropriate near vision state.

5. The spectacle wearing parameter measurement apparatus according to claim 1,
   wherein, of the spectacle wearing parameter, the distance vision spectacle wearing distance and the near vision spectacle wearing distance are measured by a calculation in consideration of a three dimensional shape of the spectacle frame.

6. The spectacle wearing parameter measurement apparatus according to claim 1,
   wherein, of the spectacle wearing parameter, the near vision inter-pupil distance is measured by a calculation on a spectacle lens surface of the spectacle worn by the spectacle wearer.

7. The spectacle wearing parameter measurement apparatus according to claim 1,
   wherein a vision fixing beam in a distance vision state set by said vision fixing means is formed as a virtual image.

8. The spectacle wearing parameter measurement apparatus according to claim 1,
   wherein said measurement and calculation means detects a blinking of the spectacle wearer and takes an image of the spectacle wearer when the spectacle wearer gazes unblinkingly.

9. A spectacle lens manufactured through optical designing using a spectacle wearing parameter measured by the spectacle wearing parameter measurement apparatus described in claim 1.

10. A spectacle manufactured using a spectacle wearing parameter measured by the spectacle wearing parameter measurement apparatus described in claim 1.

* * * * *